US010182800B2

(12) United States Patent
Uchida et al.

(10) Patent No.: US 10,182,800 B2
(45) Date of Patent: *Jan. 22, 2019

(54) APPARATUS AND METHODS FOR SEALING A VASCULAR PUNCTURE

(75) Inventors: Andy H. Uchida, Los Altos, CA (US); Anthony P. Spizuoco, San Francisco, CA (US); Kevin To, San Jose, CA (US); Florencia Lim, Union City, CA (US); Scott R. Sershen, Redwood City, CA (US)

(73) Assignee: ACCESS CLOSURE, INC., Santa Clara, CA (US)

( * ) Notice: Subject to any disclaimer, the term of this patent is extended or adjusted under 35 U.S.C. 154(b) by 130 days.

This patent is subject to a terminal disclaimer.

(21) Appl. No.: 13/354,278

(22) Filed: Jan. 19, 2012

(65) Prior Publication Data

US 2012/0209323 A1    Aug. 16, 2012

Related U.S. Application Data

(60) Provisional application No. 61/434,412, filed on Jan. 19, 2011.

(51) Int. Cl.
*A61B 17/00* (2006.01)
*A61L 24/02* (2006.01)
*C08L 71/02* (2006.01)
*A61B 17/22* (2006.01)
*A61B 90/90* (2016.01)

(52) U.S. Cl.
CPC .......... *A61B 17/0057* (2013.01); *A61L 24/02* (2013.01); *C08L 71/02* (2013.01); *A61B 90/90* (2016.02); *A61B 2017/0065* (2013.01); *A61B 2017/00495* (2013.01); *A61B 2017/00526* (2013.01); *A61B 2017/00561* (2013.01); *A61B 2017/00871* (2013.01); *A61B 2017/00884* (2013.01); *A61B 2017/00889* (2013.01); *A61B 2017/00893* (2013.01); *A61B 2017/00898* (2013.01); *A61B 2017/00951* (2013.01); *A61B 2017/22067* (2013.01); *A61B 2017/22069* (2013.01)

(58) Field of Classification Search
CPC combination set(s) only.
See application file for complete search history.

(56) References Cited

U.S. PATENT DOCUMENTS

| 2,115,492 | A | 4/1938 | Kober |
| 3,765,419 | A | 10/1973 | Usher |
| 4,002,173 | A | 1/1977 | Manning |
| 4,260,077 | A | 4/1981 | Schroeder |
| 4,327,709 | A | 5/1982 | Hanson et al. |
| 4,362,150 | A | 12/1982 | Lombardi, Jr. et al. |
| 4,472,542 | A | 9/1984 | Nambu |
| 4,540,404 | A | 9/1985 | Wolvek |
| 4,655,211 | A | 4/1987 | Sakamoto et al. |
| 4,664,857 | A | 5/1987 | Nambu |
| 4,734,097 | A | 3/1988 | Tanabe |
| 4,738,658 | A | 4/1988 | Magro et al. |
| 4,838,280 | A | 6/1989 | Haaga |
| 4,852,568 | A | 8/1989 | Kensey |
| 4,890,612 | A | 1/1990 | Kensey |
| 5,061,274 | A | 10/1991 | Kensey |
| 5,104,375 | A | 4/1992 | Wolf et al. |
| 5,104,389 | A | 4/1992 | Deem et al. |
| 5,108,421 | A | 4/1992 | Fowler |
| 5,192,300 | A | 3/1993 | Fowler |
| 5,192,302 | A | 3/1993 | Kensey et al. |
| 5,221,259 | A | 6/1993 | Weldom et al. |
| 5,258,042 | A | 11/1993 | Mehta |
| 5,259,835 | A | 11/1993 | Clark et al. |
| 5,275,616 | A | 1/1994 | Fowler |
| 5,290,310 | A | 3/1994 | Makower et al. |

(Continued)

FOREIGN PATENT DOCUMENTS

| EP | 0476178 A1 | 3/1992 |
| EP | 0482350 B1 | 4/1992 |

(Continued)

OTHER PUBLICATIONS

PCT International Search Report and Written Opinion for PCT/US2012/021920, Applicant: AccessClosure, Inc., Forms PCT/ISA/220, PCT/ISA/210, and PCT/ISA/237; dated Sep. 21, 2012, 15 pages.
David, Shaun L., Office Action dated Mar. 26, 2014 in U.S. Appl. No. 12/773,326, pp. 1-14.
Fossen, Kayla J., Response to Office Action dated Jun. 26, 2014 in U.S. Appl. No. 12/773,326, pp. 1-11.
David, Shaun L., Final Office Action dated Oct. 22, 2014 in U.S. Appl. No. 12/773,326, pp. 1-13.
Gel (definition), Wikipedia, http://en.wikipedia.org/wiki/Gel, 1 page, Mar. 23, 2014.
Communication from the Examining Division and Annex to the communication for European Application No. 12737125, dated Apr. 16, 2015, 5 pages.
Communication from the Examining Division and Annex to the communication for European Application No. 12737125, dated Feb. 4, 2016, 5 pages.

(Continued)

*Primary Examiner* — Robert S Cabral
(74) *Attorney, Agent, or Firm* — Amanda F. Maharaj

(57) ABSTRACT

A sealant is provided for sealing a puncture through tissue that includes an elongate first section including a proximal end, a distal end, and a cross-section sized for delivery into a puncture through tissue, and a second section fused to and extending from the distal end of the first section. The first section may be formed from a freeze-dried hydrogel that expands when exposed to physiological fluid within a puncture. The second section may be formed from a solid mass of non-freeze-dried, non-crosslinked hydrogel precursors, the precursors remaining in an unreactive state until exposed to an aqueous physiological, whereupon the precursors undergo in-situ crosslinking with one another to provide an adhesive layer bonded to the first section. Apparatus and methods for delivering the sealant into a puncture through tissue are also provided.

22 Claims, 15 Drawing Sheets

(56) References Cited

U.S. PATENT DOCUMENTS

| | | | |
|---|---|---|---|
| 5,292,332 A | 3/1994 | Lee | |
| 5,306,254 A | 4/1994 | Nash et al. | |
| 5,320,639 A | 6/1994 | Rudnick | |
| 5,324,306 A | 6/1994 | Makower et al. | |
| 5,334,216 A | 8/1994 | Vidal | |
| 5,383,896 A | 1/1995 | Gershony | |
| RE34,866 E | 2/1995 | Kensey et al. | |
| 5,391,183 A | 2/1995 | Janzen et al. | |
| 5,409,703 A | 4/1995 | McAnalley | |
| 5,413,571 A | 5/1995 | Katsaros et al. | |
| 5,419,765 A | 5/1995 | Weldon et al. | |
| 5,431,639 A | 7/1995 | Shaw | |
| 5,437,292 A | 8/1995 | Kipshidze et al. | |
| 5,437,631 A | 8/1995 | Janzen | |
| 5,441,517 A | 8/1995 | Kensey et al. | |
| 5,443,481 A | 8/1995 | Lee | |
| 5,464,396 A | 11/1995 | Barta et al. | |
| 5,486,195 A | 1/1996 | Myers et al. | |
| 5,489,278 A | 2/1996 | Abrahamson | |
| 5,514,158 A | 5/1996 | Kanesaka | |
| 5,529,577 A | 6/1996 | Hammerslag | |
| 5,550,187 A | 8/1996 | Rhee | |
| 5,571,181 A | 11/1996 | Li | |
| 5,580,923 A | 12/1996 | Yeung | |
| 5,591,204 A | 1/1997 | Jansen et al. | |
| 5,591,205 A | 1/1997 | Fowler | |
| 5,601,602 A | 2/1997 | Fowler | |
| 5,626,601 A | 5/1997 | Gershony et al. | |
| 5,643,464 A | 7/1997 | Rhee | |
| 5,660,849 A | 8/1997 | Poison et al. | |
| 5,700,477 A | 12/1997 | Rosenthal | |
| 5,716,375 A | 2/1998 | Fowler | |
| 5,718,916 A | 2/1998 | Scherr | |
| 5,725,498 A | 3/1998 | Janzen | |
| 5,725,551 A | 3/1998 | Myers et al. | |
| 5,728,122 A | 3/1998 | Leschinsky et al. | |
| 5,731,368 A | 3/1998 | Stanley et al. | |
| 5,741,223 A | 4/1998 | Janzen et al. | |
| 5,744,153 A | 4/1998 | Yewey et al. | |
| 5,752,974 A | 5/1998 | Rhee et al. | |
| 5,780,044 A | 7/1998 | Yewey et al. | |
| 5,782,860 A | 7/1998 | Epstein et al. | |
| 5,785,679 A | 7/1998 | Abolfathi et al. | |
| 5,795,331 A | 8/1998 | Cragg et al. | |
| 5,830,130 A | 11/1998 | Janzen et al. | |
| 5,836,970 A | 11/1998 | Pandit | |
| 5,843,124 A | 12/1998 | Hammerslag | |
| 5,916,236 A | 6/1999 | Muijs Van de Moer et al. | |
| 5,922,009 A | 7/1999 | Epstein et al. | |
| 5,928,266 A | 7/1999 | Kontos | |
| 5,941,847 A | 8/1999 | Huber et al. | |
| 5,948,429 A | 9/1999 | Bell | |
| 5,948,829 A | 9/1999 | Wallajapet | |
| 5,951,583 A | 9/1999 | Jensen et al. | |
| 5,951,589 A | 9/1999 | Epstein et al. | |
| 5,957,952 A | 9/1999 | Gershony | |
| 5,972,375 A | 10/1999 | Truter | |
| 5,973,014 A | 10/1999 | Funk | |
| 6,017,359 A | 1/2000 | Gershony | |
| 6,022,361 A | 2/2000 | Epstein et al. | |
| 6,027,471 A | 2/2000 | Fallon et al. | |
| 6,045,570 A | 4/2000 | Epstein et al. | |
| 6,048,358 A | 4/2000 | Barak | |
| 6,051,248 A | 4/2000 | Sawhney | |
| 6,056,768 A | 5/2000 | Cates | |
| 6,056,769 A | 5/2000 | Epstein et al. | |
| 6,063,061 A | 5/2000 | Wallace | |
| 6,083,522 A | 7/2000 | Chu | |
| 6,093,388 A | 7/2000 | Ferguson | |
| 6,152,943 A | 11/2000 | Sawhney | |
| 6,162,240 A | 12/2000 | Cates et al. | |
| 6,162,241 A | 12/2000 | Coury et al. | |
| 6,165,201 A | 12/2000 | Sawhney | |
| 6,179,862 B1 | 1/2001 | Sawhney | |
| 6,238,412 B1 | 5/2001 | Dubrul et al. | |
| 6,271,278 B1 | 8/2001 | Park | |
| 6,287,323 B1 | 9/2001 | Hammerslag | |
| 6,296,658 B1 | 10/2001 | Gershony | |
| 6,299,597 B1 | 10/2001 | Buscemi et al. | |
| 6,302,898 B1 | 10/2001 | Edwards et al. | |
| 6,350,274 B1 | 2/2002 | Li | |
| 6,368,300 B1 | 4/2002 | Fallon et al. | |
| 6,371,975 B2 | 4/2002 | Cruise et al. | |
| 6,379,373 B1 | 4/2002 | Sawhney | |
| 6,458,147 B1 | 10/2002 | Cruise et al. | |
| 6,475,177 B1 | 11/2002 | Suzuki | |
| 6,514,534 B1 | 2/2003 | Sawhney | |
| 6,562,059 B2 | 5/2003 | Edwards et al. | |
| 6,566,406 B1 | 5/2003 | Pathak | |
| 6,569,185 B2 | 5/2003 | Ungs | |
| 6,605,294 B2 | 8/2003 | Sawhney | |
| 6,608,117 B1 | 8/2003 | Gvozdic | |
| 6,613,070 B2 | 9/2003 | Redmond et al. | |
| 6,635,068 B1 | 10/2003 | Dubrul et al. | |
| 6,689,148 B2 | 2/2004 | Sawhney | |
| 6,699,261 B1 | 3/2004 | Cates et al. | |
| 6,703,047 B2 | 3/2004 | Sawhney | |
| 6,774,151 B2 | 8/2004 | Malmgren | |
| 6,818,008 B1 | 11/2004 | Cates | |
| 6,818,018 B1 | 11/2004 | Sawhney | |
| 6,863,924 B2 | 3/2005 | Ranganathan | |
| 6,887,974 B2 | 5/2005 | Pathak | |
| 6,960,617 B2 | 11/2005 | Omidian | |
| 7,316,704 B2 | 1/2008 | Bagaoisan et al. | |
| 7,335,220 B2 * | 2/2008 | Khosravi | A61B 17/00491 606/213 |
| 7,780,980 B2 | 8/2010 | Sawhney | |
| 7,790,192 B2 | 9/2010 | Khosravi et al. | |
| 7,806,856 B2 | 10/2010 | Bagaoisan et al. | |
| 7,993,367 B2 | 8/2011 | Bagaoisan et al. | |
| 8,002,742 B2 | 8/2011 | Pai et al. | |
| 8,029,533 B2 | 10/2011 | Bagaoisan et al. | |
| 8,292,918 B2 | 10/2012 | Hill et al. | |
| 8,394,122 B2 | 3/2013 | Bagaoisan et al. | |
| 8,617,204 B2 | 12/2013 | Khosravi et al. | |
| 8,795,709 B2 | 8/2014 | Sawhney et al. | |
| 9,820,728 B2 | 11/2017 | Mylonakis et al. | |
| 2001/0031948 A1 | 10/2001 | Cruise et al. | |
| 2001/0046518 A1 | 11/2001 | Sawhney | |
| 2001/0047187 A1 | 11/2001 | Milo et al. | |
| 2001/0051813 A1 | 12/2001 | Hnojewyj | |
| 2002/0015724 A1 | 2/2002 | Yang et al. | |
| 2002/0062104 A1 | 5/2002 | Ashby et al. | |
| 2002/0072767 A1 | 6/2002 | Zhu | |
| 2002/0106409 A1 | 8/2002 | Sawhney et al. | |
| 2002/0111392 A1 | 8/2002 | Cruise | |
| 2002/0111851 A1 | 8/2002 | Ungs | |
| 2002/0120228 A1 | 8/2002 | Maa et al. | |
| 2002/0188319 A1 | 12/2002 | Morris et al. | |
| 2003/0008831 A1 | 1/2003 | Yang et al. | |
| 2003/0012734 A1 | 1/2003 | Pathak | |
| 2003/0014075 A1 | 1/2003 | Rosenbluth et al. | |
| 2003/0061735 A1 | 3/2003 | Pavcnick et al. | |
| 2003/0078616 A1 | 4/2003 | Ginn et al. | |
| 2003/0088269 A1 | 5/2003 | Ashby | |
| 2003/0088271 A1 | 5/2003 | Cragg et al. | |
| 2003/0100921 A1 | 5/2003 | Addis et al. | |
| 2003/0135234 A1 | 7/2003 | Fisher et al. | |
| 2003/0135236 A1 | 7/2003 | Fisher et al. | |
| 2003/0139770 A1 | 7/2003 | Fisher et al. | |
| 2003/0139771 A1 | 7/2003 | Fisher et al. | |
| 2003/0139772 A1 | 7/2003 | Fisher et al. | |
| 2003/0139773 A1 | 7/2003 | Fisher et al. | |
| 2003/0233120 A1 | 12/2003 | Akerfeidt | |
| 2004/0063206 A1 | 4/2004 | Rowley et al. | |
| 2004/0093015 A1 | 5/2004 | Ogle | |
| 2004/0121905 A1 | 6/2004 | Ranganathan et al. | |
| 2004/0122350 A1 | 6/2004 | Zhong et al. | |
| 2004/0147016 A1 | 7/2004 | Rowley | |
| 2004/0249342 A1 | 12/2004 | Khosravi | |
| 2004/0267308 A1 | 12/2004 | Bagaoisan et al. | |
| 2005/0169882 A1 | 8/2005 | Lowe et al. | |
| 2006/0034930 A1 | 2/2006 | Khosravi et al. | |
| 2006/0079599 A1 | 4/2006 | Arthur | |

(56) References Cited

U.S. PATENT DOCUMENTS

| | | |
|---|---|---|
| 2006/0100664 A1 | 5/2006 | Pai |
| 2007/0060950 A1 | 3/2007 | Khosravi et al. |
| 2007/0231366 A1* | 10/2007 | Sawhney ............ A61L 24/0031 424/426 |
| 2008/0015709 A1 | 1/2008 | Evans et al. |
| 2009/0088793 A1 | 4/2009 | Bagaoisan et al. |
| 2010/0209478 A1 | 8/2010 | Sawhney et al. |
| 2010/0274280 A1 | 10/2010 | Sawhney |
| 2010/0280546 A1 | 11/2010 | Campbell |
| 2013/0060279 A1 | 3/2013 | Yassinzadeh |
| 2013/0226229 A1 | 8/2013 | Uchida et al. |
| 2014/0249575 A1 | 9/2014 | Mylonakis et al. |
| 2018/0028166 A1 | 2/2018 | Mylonakis et al. |

FOREIGN PATENT DOCUMENTS

| | | |
|---|---|---|
| WO | 9222252 | 12/1992 |
| WO | 9413210 A1 | 6/1994 |
| WO | 9922646 A1 | 5/1999 |
| WO | 0014155 | 3/2000 |
| WO | 0019912 | 4/2001 |
| WO | 03009764 A1 | 2/2003 |
| WO | 03087254 A2 | 10/2003 |
| WO | 03004749 | 11/2003 |
| WO | 2009025836 A1 | 2/2009 |
| WO | 2011057131 A1 | 5/2011 |

OTHER PUBLICATIONS

Communication from the Examining Division and Annex to the communication for European Application No. 12737125, dated Jun. 7, 2017, 4 pages.
Communication from the Examining Division and Annex to the communication for European Application No. 12737125, dated Nov. 17, 2016, 4 pages.
Final Office Action dated Nov. 12, 2015 for U.S. Appl. No. 13/859,615, 14 pages.
Final Office Action dated Apr. 13, 2017 for U.S. Appl. No. 13/859,615, 27 pages.
Final Office Action dated Dec. 24, 2013 for U.S. Appl. No. 13/859,615, 14 pages.
Non-Final Office Action dated Aug. 11, 2016 for U.S. Appl. No. 13/859,615, 22 pages.
Non-Final Office Action dated Jul. 17, 2013 for U.S. Appl. No. 13/859,615, 11 pages.
Non-Final Office Action dated Mar. 5, 2015 for U.S. Appl. No. 13/859,615, 13 pages.
Plastic Welding; Wikipedia; https://en.wikipedia.org/wiki/Plastic_welding; accessed Apr. 6, 2017, 8 pages.

* cited by examiner

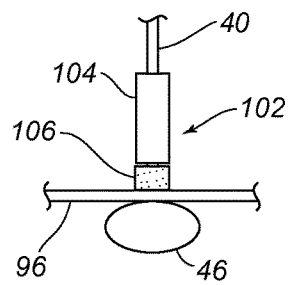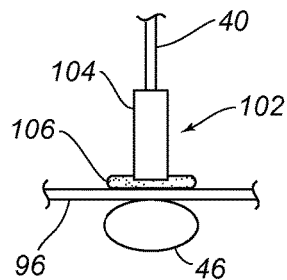
FIG. 4A  FIG. 4B
☐ Sealant
▨ Powder form of PEG-amine and PEG-ester, with or without pH modifying salts.
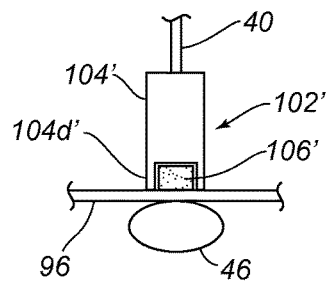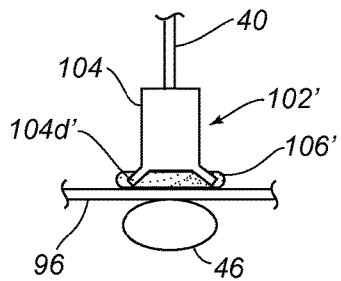
FIG. 5A  FIG. 5B
☐ Sealant
▨ Raw PEG materials
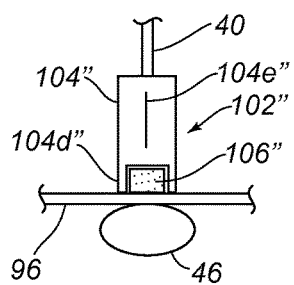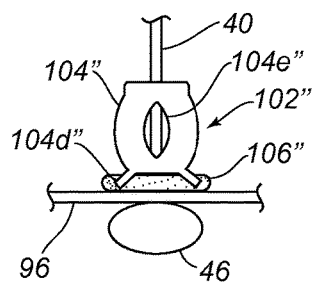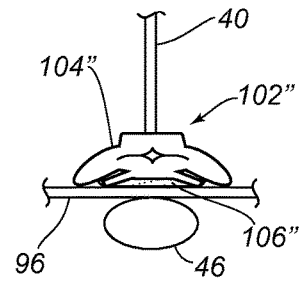
FIG. 6A  FIG. 6B  FIG. 6C
☐ Sealant
▨ Raw PEG materials ☐ Softer sealant (ex. freeze dried Mynx sealant)

▨ Harder sealant (ex. air-dried Matrix sealant, fully crosslinked & freeze dried Mynx sealant)

☐ Sealant
▨ Raw PEG materials

APPARATUS AND METHODS FOR SEALING A VASCULAR PUNCTURE

RELATED APPLICATION DATA

The present application claims benefit of U.S. provisional application Ser. No. 61/434,412, filed Jan. 19, 2011, the entire disclosure of which is expressly incorporated by reference herein.

FIELD OF THE INVENTION

The present invention relates generally to sealants, apparatus, and methods for sealing punctures in a body, and more particularly, to apparatus and methods for sealing a vascular puncture extending through tissue to a blood vessel.

BACKGROUND

Apparatus and methods are known for accessing a patient's vasculature percutaneously, e.g., to perform a procedure within the vasculature, and for sealing the puncture that results after completing the procedure. For example, a hollow needle may be inserted through a patient's skin and overlying tissue into a blood vessel. A guide wire may be passed through the needle lumen into the blood vessel, whereupon the needle may be removed. An introducer, procedural, or femoral sheath may then be advanced over the guide wire into the vessel, e.g., in conjunction with or subsequent to one or more dilators. A catheter or other device may be advanced through the introducer sheath and over the guide wire into a position for performing a medical procedure. Thus, the introducer sheath may facilitate accessing and/or introducing various devices into the vessel, while minimizing trauma to the vessel wall and/or minimizing blood loss.

Upon completing the procedure, the device(s) and introducer sheath may be removed, leaving a puncture extending between the skin and the vessel wall. To seal the puncture, external pressure may be applied to the overlying tissue, e.g., manually and/or using sandbags, until hemostasis occurs. This procedure, however, may be time consuming and expensive, requiring as much as an hour of a medical professional's time. It is also uncomfortable for the patient, and may require the patient to remain immobilized in the operating room, catheter lab, or holding area. In addition, a risk of hematoma exists from bleeding before hemostasis occurs.

Various apparatus and methods have been suggested for sealing vascular punctures resulting from such procedures, such as those disclosed in U.S. Pat. Nos. 7,316,704, 7,331,979, 7,335,220, and 7,806,856, and U.S. Publication Nos. 2007/0231366, 2008/0082122, 2009/0088793, 2009/0254110, 2010/0168789, 2010/0274280, and 2010/0280546. The entire disclosures of these references are expressly incorporated by reference herein.

For example, the MATRIX™ product included two synthetic polyethylene glycol ("PEG") polymer powders that were mixed with appropriate buffers and injected through a femoral sheath at an arteriotomy site, e.g., as disclosed in U.S. Pat. No. 7,316,704. The Mynx® Vascular Closure Device is another system for sealing vascular punctures, e.g., as disclosed in one or more of the references identified above, such as U.S. Pat. No. 7,335,220.

Accordingly, apparatus and methods for sealing a puncture through tissue would be useful.

SUMMARY

The present invention is directed to apparatus and methods for sealing a puncture in a body. More particularly, the present invention is directed to sealants for sealing a puncture through tissue, and to methods for making such sealants. In addition, the present invention is directed to apparatus and methods for providing temporary or permanent hemostasis within a puncture extending through tissue, and/or to apparatus and methods for delivering a sealant into a percutaneous puncture extending from a patient's skin to a blood vessel or other body lumen.

In accordance with one embodiment, a sealant is provided for sealing a puncture through tissue that includes a first section including a proximal end, a distal end, and a cross-section sized for delivery into a puncture through tissue, and a second section fused to and extending from the distal end of the first section. The first section may be formed from a freeze-dried hydrogel that expands when exposed to physiological fluid within a puncture. The second section may be formed from a solid mass of non-freeze-dried, non-crosslinked hydrogel precursors, the precursors remaining in an unreactive state until exposed to an aqueous physiological, whereupon the precursors undergo in-situ crosslinking with one another to provide an improved adhesion of the sealant to the arteriotomy.

In one embodiment, the first section may consist essentially of freeze-dried hydrogel, and the second section may consist essentially of the non-crosslinked precursors. Alternatively, the second section may include one or more reinforcement elements, e.g., a plurality of filaments or particles, mixed with, embedded in, or surrounding the precursors. In addition or alternatively, the second section may include one or more diluents to enhance one or more properties of the second section.

Optionally, the sealant may include one or more pH adjusting agents, e.g., impregnated into, coated over, or otherwise included in the first and/or section sections. For example, when the sealant is exposed within a puncture, the agent(s) may alter the localized pH on or around the sealant, e.g., to enhance cross-linking of the precursors and/or creation of a desired adhesive material. Alternatively, the materials for the precursors may be selected such that the pH and/or buffering capacity of interstitial body fluids and/or blood are effective to drive or facilitate cross-linking of the precursors and the pH adjusting agents may be omitted.

In accordance with another embodiment, a sealant is provided for sealing a puncture through tissue that includes an elongate first section including a proximal end, a distal end, and a cross-section sized for delivery into a puncture through tissue, the first section consisting essentially of a freeze-dried hydrogel that expands when exposed to physiological fluid within a puncture; and a second section fused to and extending from the distal end of the first section, the second section consisting essentially of a solid mass of non-freeze-dried, non-crosslinked hydrogel precursors, the precursors remaining in an unreactive state until exposed to an aqueous physiological environment, whereupon the precursors undergo in-situ crosslinking to provide an adhesive layer to bond the first section relative to adjacent tissue.

In accordance with still another embodiment, a sealant is provided for sealing a puncture through tissue that includes an elongate body including a proximal end, a distal end, and a cross-section extending between the proximal and distal ends sized for delivery into a puncture through tissue. The elongate body may consist essentially of a solid mass of non-freeze-dried, non-crosslinked hydrogel precursors, the precursors remaining in an unreactive state until exposed to an aqueous physiological environment, whereupon the precursors undergo in-situ crosslinking to provide an adhesive material that bonds to adjacent tissue within the puncture. Alternatively, the elongate body may also include one or more reinforcement members, one or more diluents, and/or one or more pH adjusting agents.

In accordance with yet another embodiment, a sealant is provided for sealing a puncture through tissue that includes a first section including a proximal end, a distal end, and a cross-section sized for delivery into a puncture through tissue, and a second section fused to and extending from the distal end of the first section. The first section may be formed from a freeze-dried hydrogel that expands when exposed to physiological fluid within a puncture. The second section may consisting essentially of a solid mass of non-freeze-dried, non-crosslinked hydrogel precursors and one or more pH adjusting agents, reinforcement elements, and/or diluents mixed with the precursors to enhance one or more mechanical properties of the second section.

In accordance with still another embodiment, a method is provided for making a sealant for sealing a puncture through tissue that includes forming an elongated first section including a proximal end, a distal end, and a cross-section sized for delivery into a puncture through tissue. The first section may be formed from a freeze-dried hydrogel or other biocompatible, bioabsorbable material that expands when exposed to physiological fluid within a puncture. A solid mass of non-crosslinked hydrogel precursors may be fused or otherwise attached onto the distal end, the precursors remaining in an unreactive state until exposed to an aqueous physiological environment, whereupon the precursors undergo in-situ crosslinking with one another to provide an improved adhesion to the arteriotomy. For example, the solid mass may be formed as a substantially uniform solid plug or may be formed as a sintered mass of powder.

In accordance with yet another embodiment, a method is provided for making a sealant for sealing a puncture through tissue that includes forming a sheet of the freeze-dried hydrogel that expands when exposed to physiological fluid within a puncture; rolling the sheet into a tubular roll including a lumen extending between the proximal and distal ends; and loading the tubular roll into a tubular member such the distal end of the tubular roll is offset inwardly from a first end of the tubular member. A plurality of non-crosslinked hydrogel precursors may be mixed and melted, optionally with one or more diluents, the precursors remaining in an unreactive state until exposed to an aqueous physiological, whereupon the precursors undergo in-situ crosslinking; The melted precursors may be applied to the distal end of the tubular roll within the tubular member, and allowed to solidify to create the solid mass fused to the distal end of the tubular roll.

In accordance with another embodiment, an apparatus is provided for sealing a puncture through tissue that includes a tubular member including a proximal end, a distal end sized for insertion into a puncture, a lumen extending between the proximal and distal ends, and a distal opening in communication with the lumen, a sealant within the lumen, and an advancer member within the lumen for deploying the sealant from the lumen out the distal opening, e.g., when the tubular member is retracted from a puncture relative to the advancer member. The sealant may include a first section including proximal and distal ends, and a second section fused to and extending from the distal end. The sealant may be disposed within the lumen such that the second section is disposed closer to the distal opening than the first section. In an exemplary embodiment, the first section may be formed from a freeze-dried hydrogel that expands when exposed to physiological fluid within a puncture, and/or the second section may be formed from non-crosslinked hydrogel precursors, the precursors remaining in an unreactive state until exposed to an aqueous physiological environment, whereupon the precursors undergo in-situ crosslinking with one another to provide improved adhesion to the arteriotomy.

In accordance with still another embodiment, a method is provided for sealing a puncture through tissue that includes providing sealant including a first section including proximal and distal ends, and a second section fused to and extending from the distal end. In an exemplary embodiment, the first section may be formed from a freeze-dried hydrogel, and/or the second section may be formed from non-crosslinked hydrogel precursors in an unreactive state. The sealant may be introduced into a puncture through tissue with the second section entering the puncture before the first section. The sealant may be exposed to fluid within the puncture, whereupon the precursors of the second section undergo in-situ crosslinking with one another to provide improved adhesion to the arteriotomy, and the freeze-dried hydrogel of the first section expands to fill space within the puncture to provide hemostasis.

Other aspects and features of the present invention will become apparent from consideration of the following description taken in conjunction with the accompanying drawings.

BRIEF DESCRIPTION OF THE DRAWINGS

It will be appreciated that the exemplary apparatus shown in the drawings are not necessarily drawn to scale, with emphasis instead being placed on illustrating the various aspects and features of the illustrated embodiments.

FIGS. 4A and 4B are side views of a first alternative embodiment of a sealant being compressed against an arteriotomy, e.g., using the apparatus and methods of FIGS. 2A-3G.

FIGS. 5A and 5B are side views of a second alternative embodiment of a sealant being compressed against an arteriotomy, e.g., using the apparatus and methods of FIGS. 2A-3G.

FIGS. 6A-6C are side views of a third alternative embodiment of a sealant being compressed against an arteriotomy, e.g., using the apparatus and methods of FIGS. 2A-3G.

DETAILED DESCRIPTION OF THE EXEMPLARY EMBODIMENTS

Figure 1:
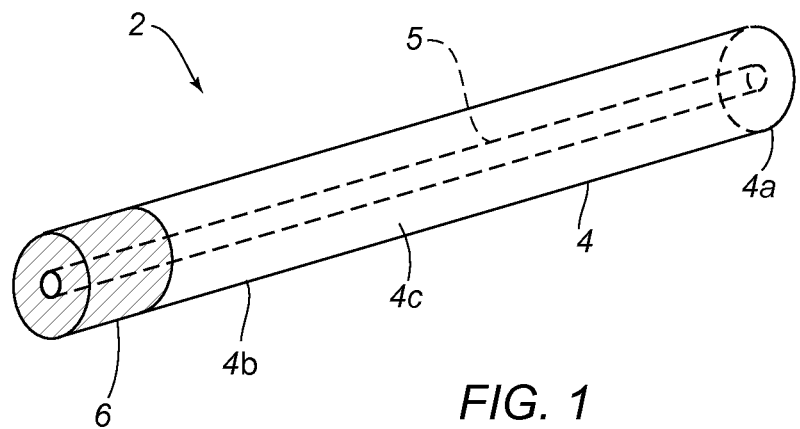
FIG. 1 is a perspective view of an exemplary embodiment of a sealant member including a main section, e.g., formed from freeze-dried hydrogel, and a distal tip section, e.g., formed from non-crosslinked precursors.

Turning to the drawings, FIG. 1 shows an exemplary embodiment of a sealant 2 for sealing a puncture extending through tissue (not shown). Generally, the sealant 2 includes a first, proximal, or main section 4 including proximal and distal ends 4a, 4b, and a second, distal, or tip section 6 formed from a plurality of non-freeze-dried and/or non-crosslinked precursors, e.g., formed as a solid mass or solid plug, fused or otherwise attached to and extending distally from the distal end 4b of the first section 4. As described further below, the non-crosslinked precursors may remain in an unreactive state, e.g., before or until exposure to an aqueous physiological environment, e.g., when deployed or otherwise exposed within a puncture extending through tissue.

For example, this configuration of sealant 2 may combine crosslinking of the second section 6 to create an adhesive material in-situ with swell characteristics of a freeze-dried hydrogel or other expandable material of the first section 4. By improving the adherence characteristics of the expandable hydrogel, the sealant 2 may provide enhanced extra-vascular closure, e.g., by providing expansion of the first section 4 in combination with improved adhesion of the sealant 2 to tissue surrounding an arteriotomy or other adjacent tissue structure, e.g., entirely extra-vascularly or extending partially into the arteriotomy and/or vessel, by virtue of the in-situ polymer crosslinking that occurs at the second section 6 of the sealant 2.

As shown, the first section 4 may be formed generally into an elongate cylindrical shape, e.g., including proximal and distal ends 4a, 4b, and an outer surface 4c extending therebetween. Optionally, as shown in phantom, the sealant 2 may include a lumen 5 extending between the proximal and distal ends 4a, 4b of the first section 4 and through the second section 6, e.g., to facilitate delivery of the sealant 2. For example, the lumen 5 may be dimensioned to accommodate receiving a balloon catheter or other positioning member 14 (not shown, see, e.g., FIGS. 2A-2C and associated description below) therethrough, e.g., such that the sealant 2 may slide relative to or pass over the positioning member 14 and/or the positioning member 14 may be directed axially relative to the sealant 2, as described further below. Alternatively, the sealant 2 may be a substantially continuous rod of material, e.g., such that the sealant 2 may be delivered into a puncture using a cartridge or shuttle without a positioning member (not shown).

In an exemplary embodiment, the first section 4 may be formed from a sheet of freeze-dried hydrogel rolled into a tubular shape, e.g., as disclosed in U.S. Publication No. 2007/0231336, the entire disclosure of which is expressly incorporated by reference herein. It will be appreciated that the first section 4 may have other tubular or solid rod cross-sections or shapes, as desired, such as elliptical, triangular, square, conical, disk, polygonic shapes, and the like (not shown).

In exemplary embodiments, the sealant 2 may have an overall length between about three and twenty millimeters (3-20 mm), e.g., between about five and ten millimeters (5-10 mm) or between about fifteen and twenty millimeters (15-20 mm), and an outer diameter or other cross-section between about one and eight millimeters (1-8 mm), e.g., between about one and three millimeters (1-3 mm), e.g., between about 1.5 and two millimeters (1.5-2.0 mm), e.g., about 0.069 inch (1.75 mm). In the embodiment shown in FIG. 1, the first section 4 is substantially longer than the second section 6, although it will be appreciated that, alternatively, the sections 4, 6 may have similar lengths, or the second section 6 may be longer than the first section 4. In a further alternative embodiment, the first section 4 may be omitted, and the second section 6 may provide the entire length of the sealant 2 (not shown), e.g., having a length between about three and twenty millimeters (3-20 mm).

For example, the first section 4 may have a length between about zero (if the sealant 2 is formed entirely from the second section 6) and twenty millimeters (0-20 mm), e.g., between about five and twenty millimeters (5-20 mm), e.g., about fifteen millimeters (15 mm). The second section 6 may have an outer diameter similar to the first section 4, but may have a length that is substantially shorter, e.g., between about zero (if the sealant 2 is formed entirely from the first section 4) and eight millimeters (0-8 mm), e.g., between about half and five millimeters (0.5-5.0 mm), e.g., about 1.5 millimeters.

The first section 4 may be formed from a biocompatible and/or bioabsorbable material, for example, a porous and/or bioabsorbable hydrogel, that may have desired expansion characteristics when hydrated. In one embodiment, the first section 4 may be formed entirely from a freeze-dried and crosslinked hydrogel, e.g., polyethylene glycol ("PEG"), or other synthetic material, as disclosed in U.S. Publication No. 2007/0231336, incorporated by reference above, although optionally including a transition zone (not shown) where the material of the second section 6 has penetrated partially into the distal end 4b of the first section 4, e.g., during fusion, as described further below.

For example, the PEG polymer for the hydrogel sealant may include two components of Polyethylene Glycol Hydrogel, e.g., PEG-Amine: 8A20K-NH2 and PEG-Ester: 4A10K-CM-HBA-NHS, e.g., as disclosed in the references incorporated by reference above. In an exemplary embodiment, the molar ratio of PEG-Amine/PEG-Ester may be between 1:9 (10% PEG-Amine: 90% PEG-Ester) and 9:1 (90% PEG-Amine:10% PEG-Ester), for example, about a 1:1 ratio.

In alternative embodiments, the first section 4 may be formed from other materials, such as pro-thrombotic material, e.g., including one or more biological pro-thrombotics, such as collagen, fibrin, carboxymethylcellulose, oxidized cellulose, alginates, gelatin, or other protein-based material, and/or synthetic materials, e.g., as polyglycolic acids (PGA's), polylactides (PLA's), polyvinyl alcohol (PVA), and the like. The material of the first section 4 may be at least partially absorbed by the body over time, e.g., over a period of days, weeks, or months.

Optionally, the first section 4 (and/or second section 6) may include therapeutic and/or pharmaceutical agents, e.g., to promote healing, prevent infection and/or other adverse medical events, and the like. Such agents may be embedded in the material and/or applied as one or more coatings or layers. In addition, the material of the first section 4 may have a substantially uniform composition or the composition may be varied, e.g., along its length and/or within underlying layers within the first section 4.

In an exemplary embodiment, the first section 4 may be formed entirely from freeze-dried hydrogel, e.g., initially formed as a thin sheet of freeze-dried polymer. For example, to fabricate the first section 4 from a PEG hydrogel material, PEG-amine and PEG-ester powders intended to form the hydrogel may be filled into separate vials. Phosphate and borate buffers may be made, e.g., by dissolving the sodium borate and sodium phosphate in sterile water for injection (WFI) and adjusting the pH of each solution to meet pre-established requirements. The two PEG powders may then be dissolved in their respective buffer solutions. These precursor solutions may be mixed together, poured into trays, and freeze-dried. The freeze-dried material may be subjected to a series of heat and/or humidity conditioning cycles, e.g., to complete the polymerization reaction.

Figure 1A:
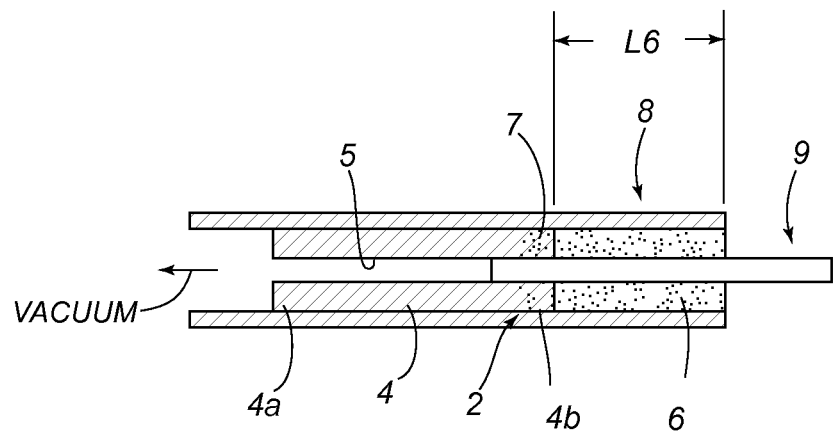
FIG. 1A is a cross-sectional view of a transfer tube and mandrel, showing a method for making the sealant member of FIG. 1.

The freeze-dried and conditioned sheet of hydrogel sealant may then be trimmed according to size and mass requirements, e.g., cut to a desired length for the finished first section 4. For example, as shown in FIG. 1A, the trimmed hydrogel may be dried, rolled, and loaded into a transfer tube 8 for subsequent attachment to the second section 6. Additional information on materials and methods for making the first section 4 may be found in U.S. Publication No. 2007/0231366, incorporated by reference above.

To fabricate the non-freeze-dried, non-crosslinked distal section 6 of the sealant 2, PEG-amine and PEG-ester powders (or other crosslinkable polymer precursors) may be melted in a beaker, mixed, and heated at a pre-determined temperature and duration. For example, the precursors may be melted in a substantially dry air or inert gas environment, e.g., to minimize or prevent entrapment of moisture, which may otherwise cause premature crosslinking Using a vacuum generator, the melted PEG may then be applied onto the distal end 4b of the rolled freeze-dried first section 4.

For example, as described above, the first section 4 may be formed from a rolled sheet and loaded into a transfer tube 8, as shown in FIG. 1A. The transfer tube 8 may have an inner diameter or other cross-section corresponding to the desired outer diameter or cross-section for the finished sealant 2. The transfer tube 8 may be formed from any material sufficient to handle the processing parameters of the assembly process, such as polymers, metals, or composite materials, and may optionally include desired coatings, e.g., PTFE to facilitate insertion of the first section 4 and/or removal of the sealant 2.

The first section 4 may be loaded into the transfer tube 8 such that the distal end 4b of the first section 4 is offset inwardly a predetermined distance L6 from the end of the transfer tube 8, e.g., corresponding to or greater than the desired length of the second section 6. For example, for a desired finished length of the second section 6 of about 1.5 millimeters, the distal end 4b may be offset inwardly about two millimeters (2.0 mm) from the end of the transfer tube 8 (with any excess material may trimmed off later, as described below). Using the vacuum generator, the melted non-crosslinked PEG is then applied onto the distal end 4b of the rolled freeze-dried sealant, e.g., the vacuum directing the melted PEG into the transfer tube 8 and against the distal end 4b of the first section 4 (as represented by the arrow labeled "vacuum"). Thus, the transfer tube 8 may mold the melted PEG into the desired shape, e.g., diameter and/or length, for the second section 6.

The vacuum may cause the melted precursors to nominally abut the distal end 4b of the first section 4, and/or may partially draw the melted precursors into the pores and/or other open spaces within the first section 4, e.g., due to capillary action and the like. In this situation, a transition zone 7 may be created within the distal end 4b of the first section 4 in which the melted precursors permeate the freeze-dried hydrogel or other material of the first section 4, which may enhance fusing the second section 6 to the first section 4. For example, the melted precursors may quickly cool under ambient conditions such that the penetration into the distal end 4b may be relatively short, e.g., resulting in a transition zone 7 of one millimeter (1 mm) or less.

The melted precursors may be dried under ambient conditions, e.g., simply allowed to cool and solidify, or alternatively, the melted and applied precursors may be exposed to desired conditions to accelerate or facilitate solidification of the melted precursors. The vacuum process effectively fuses the two sections together to provide a length of sealant 2.

If desired, the resulting sealant 2 may then be trimmed to length, as desired, e.g., for loading into a delivery apparatus, e.g., a cartridge or shuttle, such as those described further below and in the references incorporated by reference herein. For example, any excess length of the second section 6 may be removed, e.g., by mechanical cutting, laser cutting, and the like, to provide the desired length for the final second section 6. In addition or alternatively, the first section 4 may be trimmed to a desired length, e.g., by cutting the proximal end 4a before loading the first section 4 into the transfer tube 8 (as described above) and/or after fusing the second section 6 to the distal end 4b.

In addition or alternatively, if the sealant 2 and/or first section 4 includes a lumen 5, the lumen 5 may be created when the first section 4 is formed, e.g., if the first section 4 is rolled from one or more sheets or layers of material or formed by molding. Alternatively, the lumen 5 may be formed by boring into or otherwise removing material from an already formed and solid first section 4, second section 6, or through the entire sealant 2. For example, if the first section 4 is formed from a rolled sheet, a rod or other mandrel 9 (which may be fabricated similar to the transfer tube 8) may be inserted through the lumen 5 before the second section 6 is applied to the distal end 4b, e.g., that extends from the transfer tube 8, as shown in FIG. 1A. Thus, the second section 6 may be molded and fused to distal end 4b around the mandrel 9, e.g., within the transfer tube 8. The mandrel 8 may be removed once the melted precursors have solidified, resulting in a continuous lumen through the second section 6 and the first section 4. Alternatively, the portion of the lumen 5 through the second section 6 may be bored, drilled, or otherwise created after the second section 6 is formed and fused to the first section 5.

In exemplary embodiments, the precursors for the second section 6 may include one or more of the following:

a) Polyethylene glycol derivatives or polyethylene glycols with at least two end groups (2Arms) and having at least one crosslinkable end groups. The first functional groups may chemically react with the second functional groups in-situ to form covalent bonds and thereby form a crosslinkable gel.

b) The first functional groups or second functional groups may be chosen from groups that are strong electrophiles, e.g., epoxide, succinimide, N-hydroxysuccinimide, acrylate, methacrylate, maleimide, and N-hydroxysulfosuccinimide in addition to a group including amine, sulfhydryl, carboxyls, or hydroxyls.

c) The molecular weight of the polyethylene glycols may range from 5000 to 40,000 Da and may include at least about 2 to 8 functional groups.

d) Examples of the polyethylene glycols derivatives that may be used include but are not limited to the following formulations:

i) Branched PEG Derivatives:
Y-Shape PEG NHS Ester, MW 40000
Y-Shape PEG Maleimide, MW 40000
Y-Shape PEG Acetaldehyde, MW 40000
Y-Shape PEG Propionaldehyde, MW 40000
ii) Heterofunctional PEG Derivatives:
Hydroxyl PEG Carboxyl, MW 3500
Hydroxyl PEG Amine, HCl Salt, MW 3500
Amine PEG Carboxyl, HCl Salt, MW 3500
Acrylate PEG NHS Ester, MW 3500
Maleimide PEG Amine, TFA Salt, MW 3500
Maleimide PEG NHS Ester, MW 3500
4 Arm PEG Succinimidyl Succinate (pentaerythritol), MW 10 KDa
8 Arms PEG Amine, MW 10-20 KDa
iii) Linear Monofunctional PEG Derivatives:
Methoxy PEG Succinimidyl Carboxymethyl Ester, MW 10-20K
Methoxy PEG Maleimide, MW 10-20K
Methoxy PEG Vinylsulfone, MW 10-20K
Methoxy PEG Thiol, MW 10-20K
Methoxy PEG Propionaldehyde, MW 10-20K
Methoxy PEG Amine, HCl Salt, MW 10-20K Optionally, the second section may include one or more pH adjusting agents. For example, a pH adjusting agent, e.g., sodium borate, sodium phosphate, sodium bicarbonate, and/or other salts, such as $Na_2B_4O_7 \cdot 10H_2O$ in crystalline or powder form, may be melted with the precursors and then applied with the precursors to the distal end 4b of the first section 4, as described above. Alternatively, the pH adjusting agent may be applied to the second section 6 after fusing the melted precursors to the first section 4, e.g., by bonding or impregnating crystals of borate or other salts to the outer surface of the solid mass of non-crosslinked precursors and/or by melting and applying a coating of melted salts to the outer surface, e.g., similar to embodiments disclosed in the references incorporated by reference elsewhere herein. In addition or alternatively, one or more pH adjusting agents may be provided on the first section 4, if desired.

In this manner, the pH adjusting agent may alter the localized pH on or around the sealant 2, e.g., when deployed within a puncture to enhance cross-linking and/or creation of a desired adhesive material. Alternatively, the pH and/or buffering capacity of interstitial body fluids and/or blood may be effective to drive or facilitate cross-linking of the second section 6. For example, the precursors of the second section 6 may be optimized to take into account all of these factors and/or form a robust attachment to tissue.

In addition or alternatively, diluents, such as low molecular PEG and/or glycerol, may be added to the formulation, i.e., the melted precursors before application to the first section 4, e.g., to improve the mechanical strength and/or integrity of the first section 6 and/or to minimize the brittleness of the second section 6.

Figure 12A:
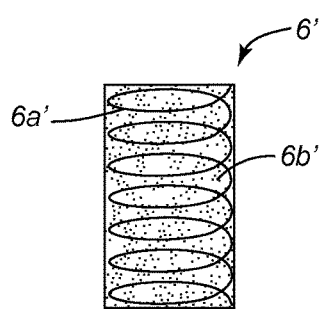
FIGS. 12A and 12B are side views of alternative embodiments of non-crosslinked precursor sections that may be provided on a sealant, such as that shown in FIG. 1.

In a further alternative, if desired, one or more reinforcement elements may be provided within the second section 6. For example, as shown in FIG. 12A, a bioabsorbable mesh 6a' may be embedded within and/or surround the precursors 6b' of a second section 6.' The mesh 6a' of bioabsorbable material may have greater rigidity, elasticity, and/or other desired properties than the solidified precursors 6b.' Exemplary materials for the reinforcement elements may include any of the bioabsorbable materials described above for the first section 4.

As shown, the mesh 6a' may include one or more fibers or filaments having a helical configuration (one helical filament shown), or alternatively the mesh 6a' may include a braid of filaments, a rolled porous mat, and the like (not shown). In an exemplary embodiment, the mesh 6a' may be embedded in the precursors 6b' of the second section 6,' e.g., by inserting the reinforcement element(s) into the end of the transfer tube 8 (not shown, see FIG. 1A) before applying the melted precursors (not shown), as described above. Thus, as the applied precursors are drawn into the transfer tube 8 and cool (or are otherwise dried and/or solidified), the precursors 6b' may permeate through and/or surround the mesh 6a,' thereby embedding the element(s) in the second section 6.'

Figure 12B:
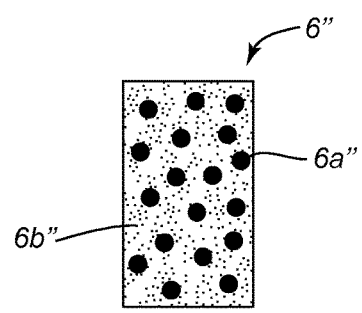

Alternatively, as shown in FIG. 12B, reinforcing particles or fillers 6a" may be provided in a second section 6." For example, similar compositions of bioabsorbable material having greater rigidity, elasticity, and/or other desired properties than the precursors 6b," such as the materials described above, may be mixed into the melted precursor mixture, and then the reinforcing fillers 6a" may be applied to the distal end 4b of the first section 4 (not shown) along with the precursors 6b," e.g., using the vacuum process described above. Thus, the filler material 6a" may be distributed randomly, substantially uniformly, or in a desired pattern throughout the second section 6," thereby enhancing the rigidity, reducing the brittleness, and/or otherwise modifying the properties of the precursors 6b" of the second section 6" in a desired manner.

Once the sealant 2 is formed and/or trimmed, as described above, the sealant 2 may be loaded onto a delivery apparatus for use in sealing a puncture, e.g., using the methods described below.

Figure 2A:
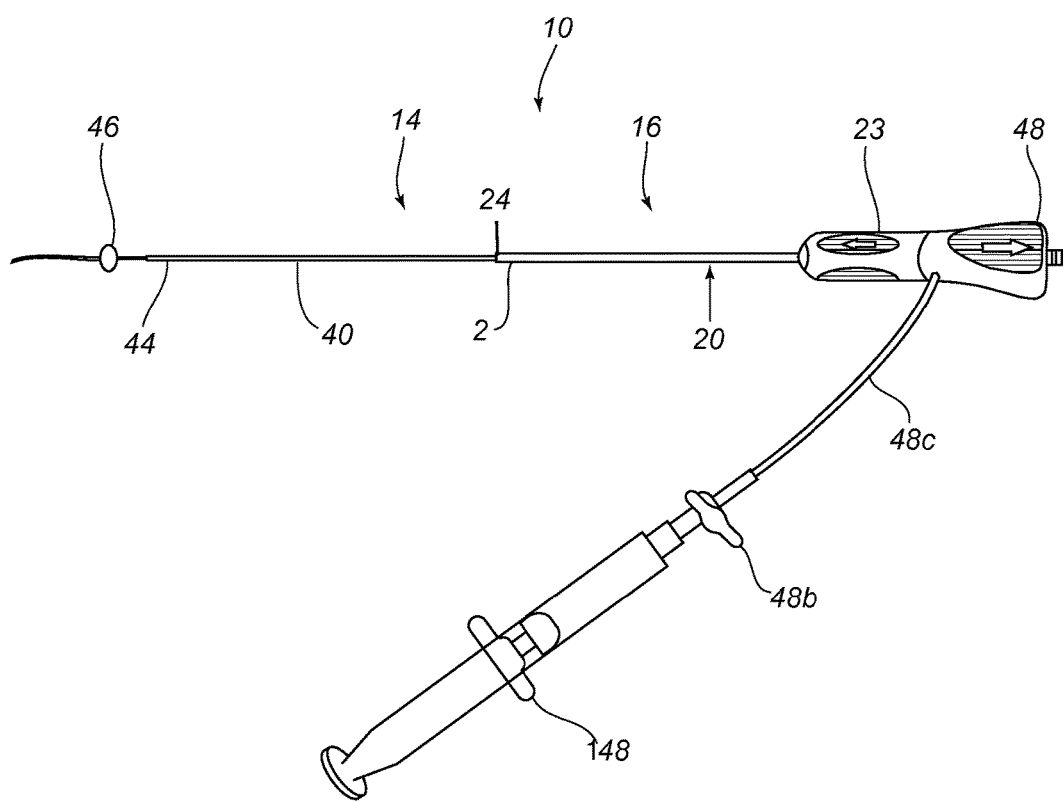
FIG. 2A is a side view of an exemplary embodiment of an apparatus for delivering a sealant into a puncture through tissue, including a positioning member, and a cartridge movable over the positioning member that includes the sealant.
Figure 2B:
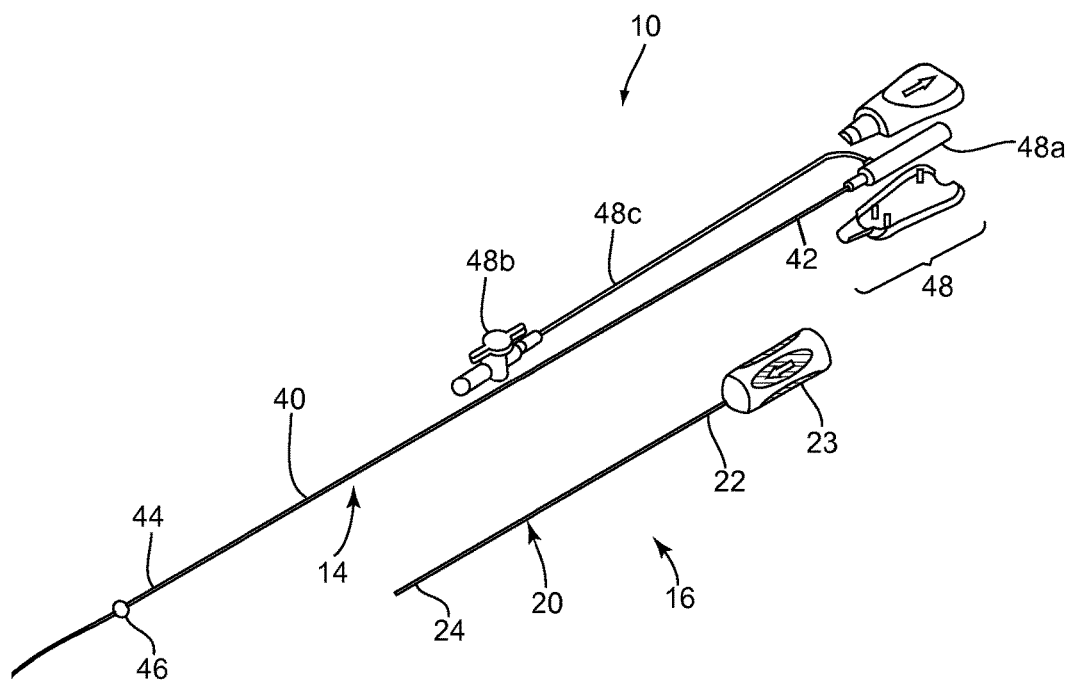
FIG. 2B is an exploded perspective view of the apparatus of FIG. 2A.
Figure 2C:
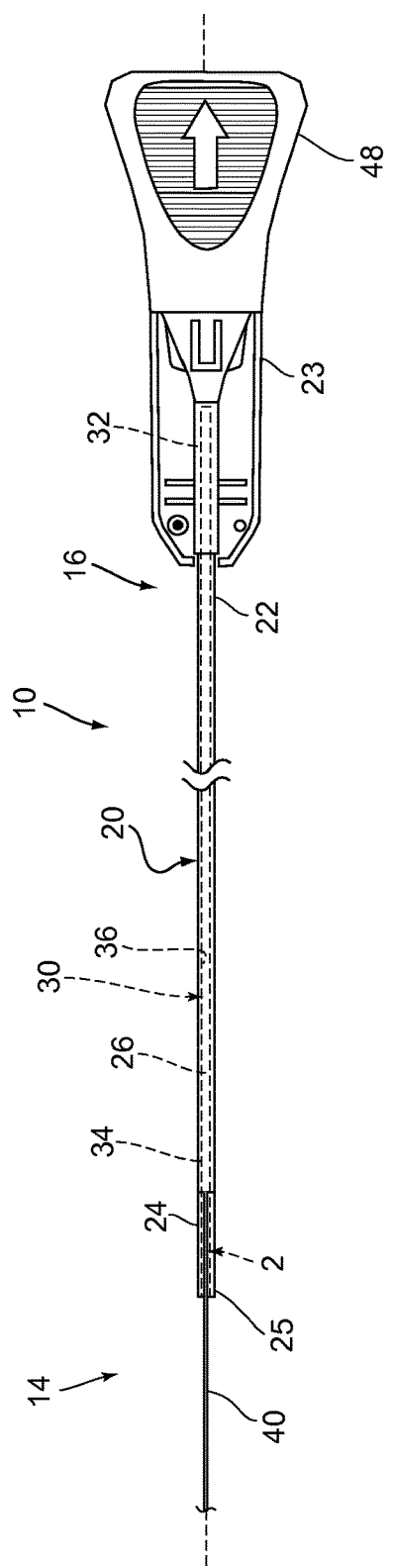
FIG. 2C is a partial cross-sectional side view of the apparatus of FIGS. 2A and 2B.

Turning to FIGS. 2A-2C, an exemplary embodiment of an apparatus 10 is shown for sealing a puncture through tissue, e.g., using the sealant 2 (or any of the other embodiments described elsewhere herein). Generally, the apparatus 10 includes a positioning member 14 and a cartridge or shuttle 16 carried on the positioning member 14 for delivering a sealant 2 therein into a puncture (not shown). Optionally, the apparatus 10 may be part of a system, e.g., which may also include a delivery, access, procedure, introducer, or other sheath 80 (not shown, see, e.g., FIGS. 3A-3F). Optionally, the apparatus 10 and/or system may include one or more other components, e.g., a needle, guidewire, and/or other instrument for creating a puncture, a source of inflation media, and/or a source of additional sealing compound (not shown), for example, to provide a kit for a medical procedure.

As shown in FIGS. 2A-2C, the cartridge 16 includes an elongate tubular member 20 carrying the sealant 2 therein, an advancer tube or member 30 adjacent the sealant 2 within the tubular member 20, and a handle or hub 23 coupled to the tubular member 20. Generally, as best seen in FIG. 2C, the tubular member 20 includes a proximal end 22 coupled to the hub 23, a distal end 24 sized for introduction into an introducer sheath and/or puncture (not shown), and a lumen 26 extending between proximal and distal ends 22, 24 of the tubular member 20. The tubular member 20 may be substantially rigid, semi-rigid, or flexible, e.g., such that the tubular member 20 may be advanced through an introducer sheath or otherwise into a puncture through tissue. Optionally, the hub 23 may include one or more detents or other features (not shown) for releasably coupling the cartridge 16 to the positioning member 14, e.g., as described in the references incorporated by reference herein.

Figure 3A:
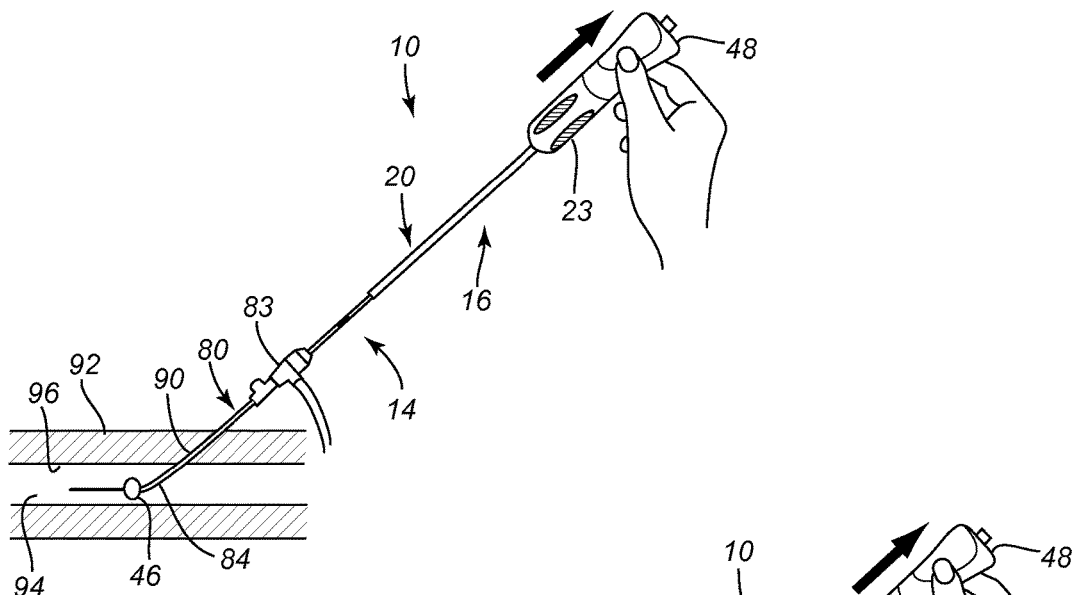
FIGS. 3A-3G are cross-sections of a patient's body showing a method for sealing a puncture using the apparatus of FIGS. 2A-2C.
Figure 3B:
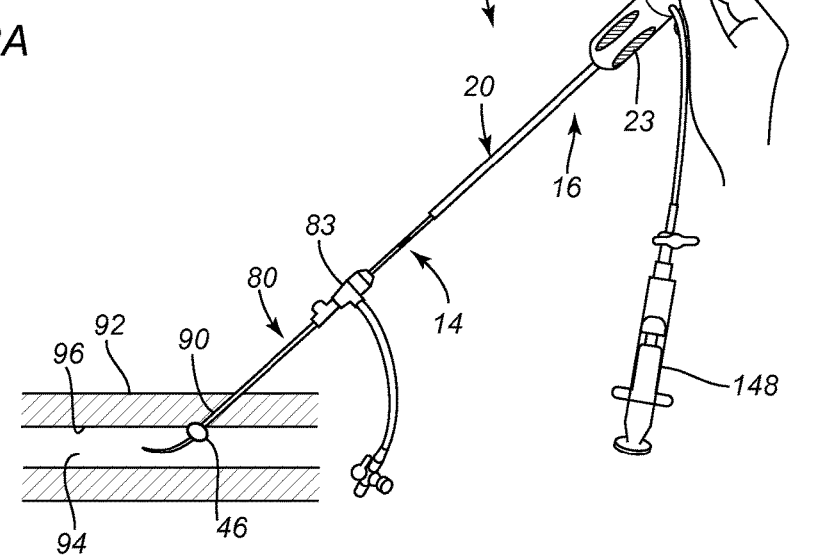
Figure 3C:
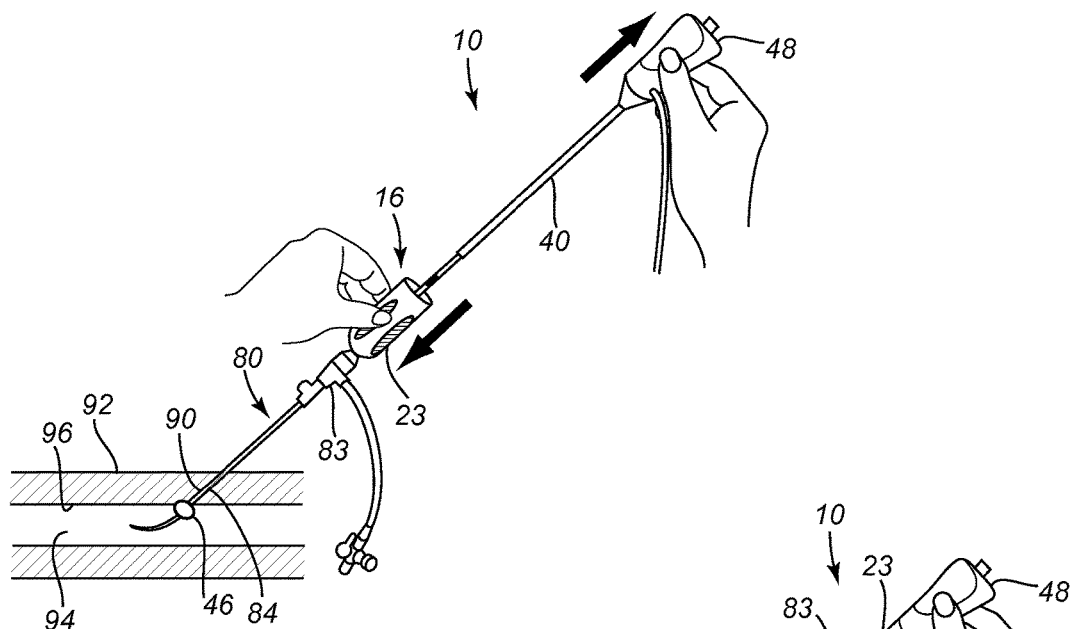
Figure 3D:
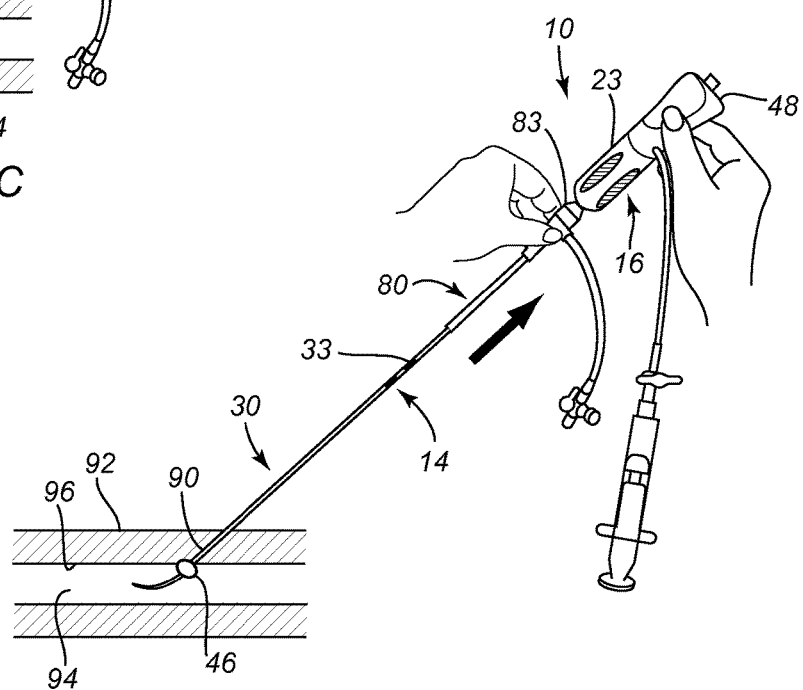
Figure 3E:
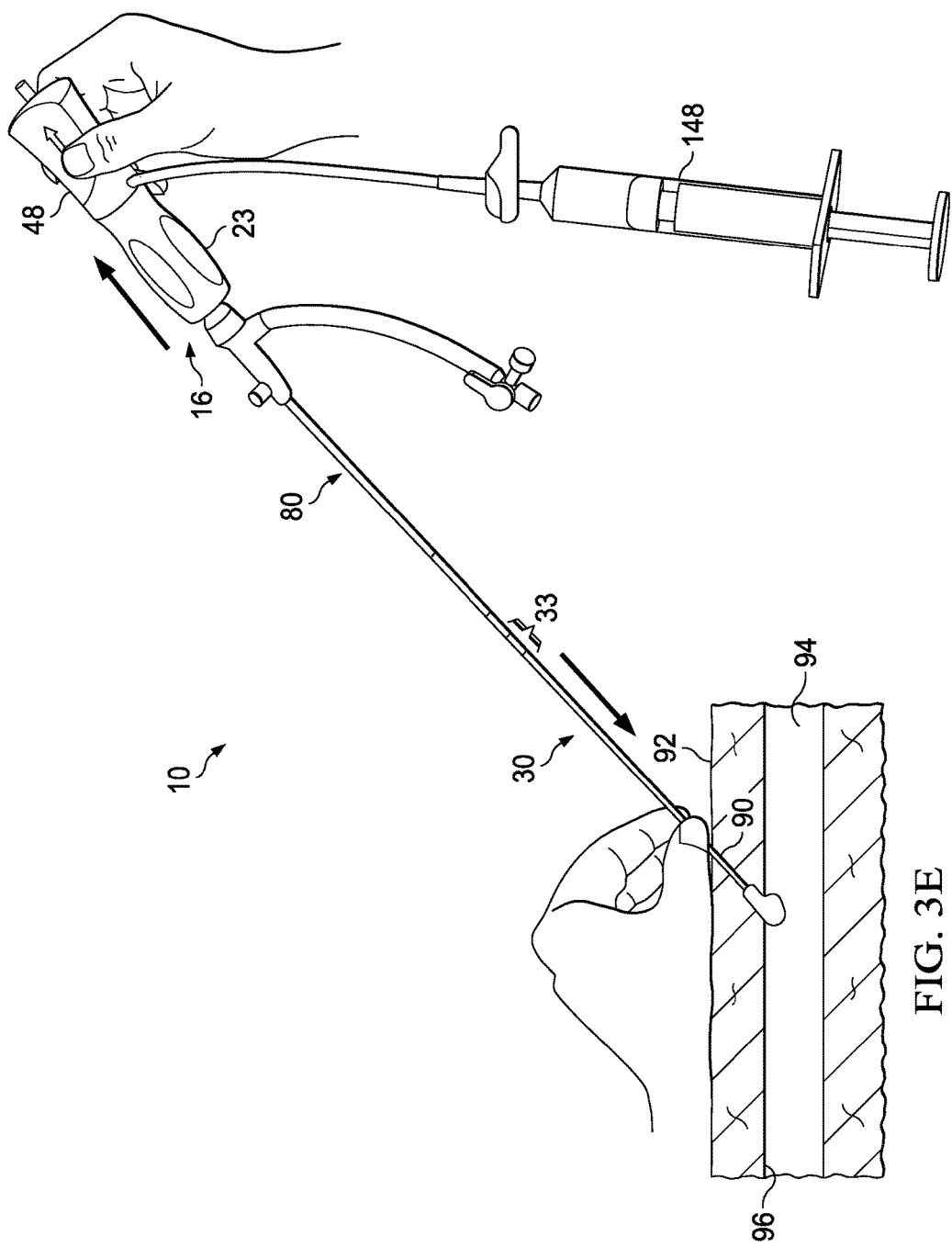
Figure 3F:
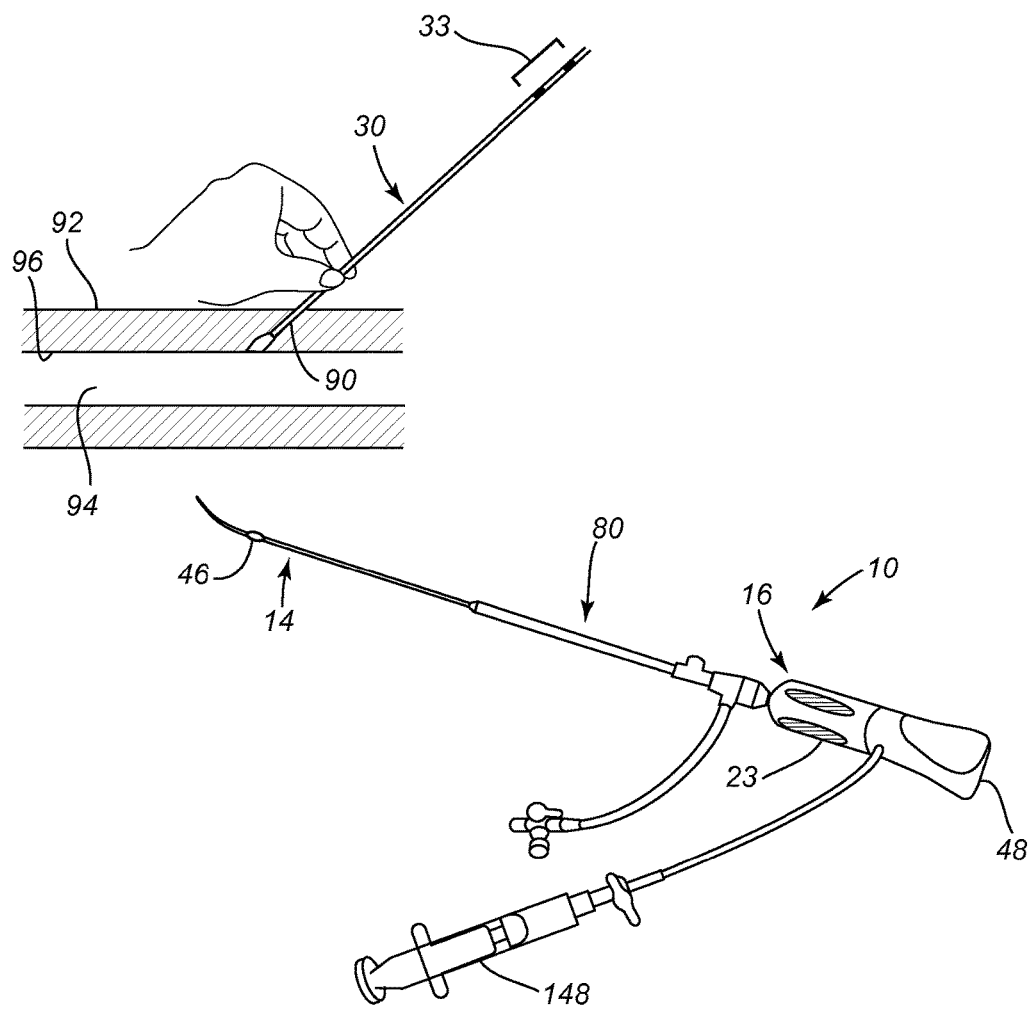

With additional reference to FIGS. 2C, 3E, and 3F, the advancer member 30 may be an elongate tubular body sized to be slidably received within the lumen 26 of the tubular member 20, although the advancer member 30 may abut or otherwise interact with the hub 23 of the cartridge 16, e.g., such that the advancer member 30 is advanced distally when the cartridge 16 is advanced. A distal end 34 of the advancer member 30 may terminate in a substantially blunt distal tip proximal to the tubular member distal end 24, as best seen in FIG. 2C, e.g., by simply cutting the end of the advancer member 30, which may facilitate contacting and/or otherwise maintaining the sealant 2 within a puncture, e.g., when the tubular member 20 is refracted during use, as described further below.

The advancer member 30 may be substantially rigid, semi-rigid, and/or substantially flexible, e.g., having sufficient column strength to allow proximal movement of the tubular member 20 relative to the sealant 2 without buckling the advancer member 30 and/or to allow the distal end 34 of the advancer member 30 to be advanced to compress the sealant 2 within a puncture, e.g., by pushing from the proximal end 32, as described further below. As best seen in FIG. 2C, the advancer member 30 may also include a lumen 36 extending between the proximal and distal ends 32, 34, e.g., to accommodate the positioning member 14, a flowable sealing compound, and/or fluid (not shown).

Optionally, the advancer member 30 may include one or more elements (not shown) on the proximal end 32, e.g., for interacting with one or more cooperating elements (also not shown) on the positioning member 14, e.g., to limit movement of the advancer member 30 relative to the positioning member 14, e.g., as described in the references incorporated by reference herein.

As shown in phantom in FIG. 2C, the sealant 2 (which, alternatively, may be any of the embodiments herein, e.g., sealant 102-502) may be disposed within the lumen 26 of the tubular member 20 proximate to the distal end 24, e.g., immediately adjacent the distal tip 25. The lumen 26 may be sized such that the tubular member 20 and sealant 2 are slidable relative to one another, e.g., to allow the tubular member 20 to be retracted proximally relative to the sealant 2 and/or advancer member 30, as described further below.

With continued reference to FIGS. 2A-2C, the positioning member 14 generally includes an elongate member 40 including a proximal end 42 (not shown, see, e.g., FIG. 2B), a distal end 44, and an occlusion or positioning element 46 on the distal end 44. The positioning element 46 may be an expandable member, such as a balloon, a wire mesh structure, an expandable frame, and the like, e.g., as disclosed in the references incorporated by reference herein. The positioning element 46 may be selectively expandable, e.g., using a source of inflation media, such as syringe 148, a pull wire, and/or other actuator (not shown), operable from the proximal end 42 of the positioning member 14.

For example, as shown, the positioning element may be a balloon 46, and the positioning member 14 may include a tubular body 40 including a lumen (not shown) extending between the proximal and distal ends 42, 44 and communicating with an interior of the balloon 46. In this embodiment, the positioning member 14 may include a source of inflation media, such as syringe 148, that may be coupled to a housing 48 on the proximal end 42 of the positioning member 14. Optionally, the positioning member 14 may include an internal pull wire (not shown) that causes the balloon 46 to shorten during expansion and extend during collapse. Exemplary embodiments of positioning members 14 including balloons that may be used are disclosed in U.S. Publication Nos. 2004/0249342, 2004/0267308, 2006/0253072, and 2008/0009794. The entire disclosures of these references are expressly incorporated by reference herein.

Alternatively, the positioning element may be biased to an enlarged condition, but may be compressed to a contracted condition, e.g., by an overlying sleeve or other constraint (not shown). The constraint may be removed to expose the positioning element, allowing the expandable element to automatically expand to the enlarged condition. Additional information on expandable structures that may be provided on the positioning member 14 may be found in U.S. Pat. Nos. 6,238,412, 6,635,068, and 6,890.343, and in co-pending application Ser. No. 10/975,205, filed Oct. 27, 2004. The entire disclosures of these references are expressly incorporated herein by reference.

With additional reference to FIGS. 3A-3G, the apparatus 10 may be used to position and deliver the sealant 2 within a puncture, e.g., extra-vascularly just above or otherwise adjacent to an arteriotomy in a blood vessel or other body lumen communicating with a puncture, as described further elsewhere herein. In one embodiment, as shown in FIGS. 2A and 3A, the cartridge 16 (along with the advancer member 30 and sealant 2 within the tubular member 20) may be initially provided on the proximal end 42 of the positioning member 14. For example, the housing 48 on the positioning member 14 and the hub 23 on the cartridge 16 may be initially connected to one another, e.g., using one or more releasable detents (not shown). Alternatively, the cartridge 16 may be initially provided such that the distal 24 of the tubular member 20 is disposed adjacent the balloon 46, e.g., as disclosed in U.S. Pat. No. 7,335,220 and U.S. Publication No. 2008/0082122, incorporated by reference elsewhere herein.

As shown in FIG. 3C, the cartridge 16 may be slidable distally along the positioning member 14, e.g., by disconnecting the hub 23 from the housing 48, and then advancing the cartridge 16, e.g., until the distal end 24 of the tubular member 20 is disposed adjacent the positioning element 46. For example, detents on the hub 23 and housing 48 may simply separate from one another when the hub 23 is advanced away from the housing 48 with sufficient force. Alternatively, one of the hub 23 and housing 48 may include an actuator or lock that may be activated (not shown) to separate the detents and/or otherwise allow the cartridge 16 to be advanced relative to the positioning member 14.

Optionally, the cartridge 16 and/or positioning member 14 may include cooperating features that limit distal movement of the cartridge 16 relative to the positioning member 14. For example, the hub 23 of the cartridge 16 may include a pocket and the positioning member 14 may include a detent or other feature (both not shown) that may be received within the pocket when the cartridge 16 is advanced to a distal position. In addition or alternatively, the positioning member 14 and/or advancer member 30 may include one or more elements that engage when the cartridge 16 reaches a predetermined location when advanced along the positioning member 14, e.g., to limit subsequent proximal movement of the advancer member 30 relative to the positioning member 14 when the tubular member 20 is subsequently retracted, similar to embodiments disclosed in the references incorporated by reference herein.

In addition or alternatively, one or more markers may be provided on the apparatus 10, e.g., to identify when components are located at one or more desired positions or otherwise to facilitate use of the apparatus 10. For example, the positioning member 14 may include one or more markers at predetermined locations on the elongate member 40. Such markers may provide visual confirmation when the cartridge 16 has been advanced to a desired distal position, e.g., when the marker(s) emerge from the hub 23 as the cartridge 16 is advanced over the positioning member 14. In addition or alternatively, as shown in FIGS. 3E and 3F, the advancer member 30 may include one or more markers 33 thereon, which may be visible when the cartridge 16 is advanced to a distal position and then the tubular member 20 is retracted to expose the sealant 2. These markers 33 may also provide visual guides to inform the user when the advancer member 30 is manipulated, e.g., advanced into a puncture to compress the sealant 2 therein, as described further below.

The apparatus 10 may be assembled using conventional manufacturing methods and/or using methods disclosed in the references incorporated by reference herein. Although an exemplary process is described below as being performed in an exemplary order, it will be appreciated that the actual order of the assembly steps may be changed, as desired.

For example, the positioning member 14 may be formed by providing a length of tubing for the tubular body 40 and attaching a balloon 46 to the distal end 44. To make the balloon, a section of tubing, e.g., LLDPE or other elastic material, may be cut to a predetermined length that is necked down to a smaller diameter, e.g., using a hot die or hot air necker. The tubing may then be placed into a balloon blower, which may use a split aluminum or other mold (not shown) to form the balloon 46, e.g., at a desired temperature and blow pressure. The resulting balloon subassembly may then be trimmed as desired and attached to the distal end 44 of the tubular body 40, which may also be necked down to facilitate attachment of the balloon 46, e.g., by an interference fit, bonding with adhesive, fusing, and the like.

The components of the cartridge 16, the tubular body 20, advancer tube 30, and hub 23 may be formed using conventional methods, e.g., extruding, molding, and the like. For example, the hub 23 may be formed from a plurality of molded shells that may be attached together and to which the proximal end 22 of the tubular body 20 may be attached.

In the exemplary embodiment shown, the cartridge 16 includes a single tubular body 20 attached to the hub 23. In an alternative embodiment, the cartridge 16 may include inner and outer cartridge assemblies, including inner and outer tubular bodies (not shown) attached to the hub 23, e.g., similar to embodiments disclosed in the references incorporated by reference herein. For example, an inner cartridge subassembly may include tubing bonded to a molded hub, and an outer cartridge subassembly may include tubing bonded to a molded slider. The inner and outer cartridges may then be captured within halves of a shuttle shell providing the hub 23.

The advancer member 30 may include a section of tubing with a thermoformed tapered tip. Once the tubular body 20 (or bodies) is assembled to the hub 23, the advancer member 30 may be inserted into the lumen 26 of the tubular body 20 (e.g., into the inner cartridge tubing if inner and outer cartridge tubular bodies are provided).

To provide the hub 48 of the positioning member 14, a hub barrel 48a, stopcock 48b, and extension line 48c may be assembled, as shown in FIG. 2B, similar to embodiments disclosed in the references incorporated by reference herein. One end of the extension line 48c may be bonded or otherwise attached to the stopcock 48b, and the other end of the extension line 48c may be bonded or otherwise attached into the side port of the hub barrel 48a.

To complete the positioning member 14, locking features (not shown) may be bonded onto the tubular body 40, e.g., spaced a predetermined distance from the proximal end 42. The proximal leg of the balloon 46 may be bonded to the distal end 44 of the tubular body 40. The cartridge 16, hub barrel 48 and a core wire with tension plunger (not shown) are all then assembled with the tubular body 40, e.g., similar to embodiments in the references incorporated by reference herein. The core wire may then be bonded into the distal leg of the balloon 46. The hub barrel 48a is bonded to the proximal end 42 of the tubular body 40 and captured within the halves of the handle shell to provide the hub 48, as shown in FIG. 2.

Finally, the sealant 2 is loaded onto the assembled apparatus 10. For example, the rolled sealant 2 may be coaxially mounted over the tubular body 40 from the distal end 44 and positioned inside the tubular member 20 of the cartridge 16, e.g., adjacent the distal end 24 and the advancer member 30 therein. For example, the sealant 2 stored within a transfer tube 8 (not shown, see FIG. 1A) may be aligned with the balloon 46 and distal end 44 of the tubular body 40 such that the proximal end 4a of the first section 4 is oriented towards the proximal end 42 of the tubular body 40. The sealant 2 may then be transferred from the transfer tube 8 over the tubular body 40 into the cartridge 20 such that the distal section 6 is located closest to the distal end 24 within the tubular member 20.

Optionally, a thin silicone coating may be applied to the tubular body 40, the tubular member 20, and the balloon 46. A protective sheath (not shown) may then be placed over the balloon 46 and at least partially over the tubular body 40.

The apparatus 10 and syringe 148 may then be placed with appropriate packaging, e.g., into respective cavities within a thermoformed clamshell tray (not shown), and the clamshell tray snaps may be closed. The closed tray may be inserted into a foil pouch or other packaging as desired. Additional processing, such as product labeling, sterilization, and the like, may be completed before the apparatus 10 is provided to a user.

Turning to FIGS. 3A-3G, an exemplary method is shown for sealing a puncture 90, e.g., using the apparatus 10 to deliver a sealant 2 (which again may be any of the exemplary embodiments herein), e.g., to achieve hemostasis within the puncture 90. Generally, the puncture 90 extends from a patient's skin 92 through intervening tissue, e.g., to a body lumen 94. In an exemplary embodiment, the puncture 90 may be a percutaneous puncture communicating with a blood vessel 94, such as a femoral artery, carotid artery, and the like.

In an exemplary method, the puncture 90 may be created using known procedures, e.g., using a needle, guidewire, one or more dilators, and the like (not shown). An introducer sheath 80 may be advanced through the puncture 90 into the vessel 94, e.g., over a guidewire (not shown) placed through the puncture 90 into the vessel 94. The introducer sheath 80 may provide access into the vessel 92 for one or more instruments (not shown), e.g., to allow one or more diagnostic and/or interventional procedures to be performed via the vessel 94. Upon completing the procedure(s) via the vessel 94, any such instrument(s) may be removed from the puncture 90, leaving the introducer sheath 80 extending through the puncture 90 into the vessel 94.

With reference to FIG. 3A, the positioning member 14 may be introduced into and/or through the lumen of the introducer sheath 80, e.g., with the expandable positioning element 46 in a collapsed condition. The cartridge 16, along with the sealant 2 and advancer member 30, may be provided initially on the proximal end 42 of the positioning member 40, e.g., as shown in FIGS. 2A and 3A. Thus, the distal end 24 of the tubular member 20 may initially be located outside the puncture 90 when the positioning member 40 is advanced into the puncture 90.

Still referring to FIG. 3A, the distal end 44 of the positioning member 14 may be inserted through the puncture 90 (via the introducer sheath 80) and into the vessel 94. Once the positioning element 46 is disposed within the vessel 94, i.e., beyond a distal end 84 of the introducer sheath 80, the positioning element 46 may be expanded to an enlarged condition, as shown.

After expanding the positioning element 46, the positioning member 40 may be at least partially withdrawn until the positioning element 46 contacts the wall of the vessel 94, e.g., to substantially seal the vessel 94 from the puncture 90. In an exemplary method, shown in FIGS. 3A and 3B, this may involve a two-step process (although it may be completed in a single substantially continuous action). First, with the positioning element 46 expanded within the vessel 94, the positioning member 14 may be withdrawn until the positioning element 46 contacts the distal end 84 of the introducer sheath 80, which may provide a first tactile feedback to the user (i.e., that the positioning element 46 has contacted the introducer sheath 80, e.g., based upon the increased weight and/or resistance to proximal movement). The positioning member 14 may be withdrawn further until the positioning element 46 contacts the wall of the vessel 94 and resists further withdrawal, thereby providing a second tactile feedback. The introducer sheath 80 may be pulled proximally by the positioning element 46 as the positioning member 14 is withdrawn, e.g., until the distal end 84 of the introducer sheath 80 is withdrawn from the vessel 94 into the puncture 90, as shown in FIG. 3B.

Proximal tension may be applied and/or maintained on the positioning member 14 to hold the positioning element 46 against the wall of the vessel 94, e.g., to seal the puncture 90 from the vessel 94 and/or prevent further removal of the positioning member 14. The proximal tension may be maintained manually or using a tensioner device (not shown) to provide temporary hemostasis, e.g., during the subsequent steps. Exemplary tension devices are disclosed in U.S. Publication No. 2004/0267308, incorporated by reference elsewhere herein.

Turning to FIG. 3C, the cartridge 16 (carrying the sealant 2) may then be advanced distally over the positioning member 14 into the puncture 90. As shown, the distal end 24 of the tubular member 20 may enter the introducer sheath 80 and be advanced towards the positioning element 46. The cartridge 16 may be advanced until a component of the cartridge 16 encounters a stop on the positioning member 14, thereby preventing further advancement of the cartridge 16 and/or spacing the sealant 2 a predetermined distance from the positioning element 46. Alternatively, the cartridge 16 may be advanced into the introducer sheath 80 until the distal end 24 contacts the expanded positioning element 46, which may provide tactile feedback that the cartridge 16 has been advanced sufficiently, or the sealant 2 is otherwise positioned within the puncture 90.

Thereafter, as shown in FIG. 3D, the tubular member 20 of the cartridge 16 and introducer sheath 80 may be refracted, e.g., by pulling proximally on a hub 83 of the introducer sheath 80, to withdrawn the introducer sheath 80 and tubular member 20 from the puncture 90 and expose the sealant 2 within the puncture 90 beyond the introducer sheath distal end 84. Optionally, a sleeve or locking device (not shown) may be provided on the cartridge 16 that may couple the introducer sheath 80 to the tubular member, similar to embodiments disclosed in U.S. Publication No. 2009/0088793, the entire disclosure of which is expressly incorporated by reference herein. Thus, in this alternative, if the user pulls proximally on the hub 23 or tubular member 20 rather than the hub 83 of the introducer sheath 80, the introducer sheath 80 and tubular member 20 may still be withdrawn together from the puncture 90.

As the tubular member 20 is retracted, the advancer member 30 may prevent substantial proximal movement of the sealant 2, thereby exposing the sealant 2 within the puncture 90, as shown in FIGS. 3D and 3E. For example, as described above, as the cartridge 16 is advanced, one or more features (not shown) on the proximal end 32 of the advancer member 30 may pass over a reduced region or other feature (also not shown) on the positioning member 14, thereby preventing subsequent proximal withdrawal of the advancer member 30 relative to the positioning member 14. Thus, when the cartridge 16 is then retracted, the features may prevent substantial proximal movement of the advancer member 30, and the sealant 2 adjacent the distal end 34 of the advancer member 30.

When the sealant 2 is exposed within the puncture 90, the sealant 2 may be exposed to blood and/or other body fluids within the puncture 90. This exposure may cause the sealant 2 to absorb fluid and activate to provide hemostasis, as described further elsewhere herein. Optionally, as shown in FIG. 3E, once the sealant 2 is exposed within the puncture 90, the advancer member 30 may be advanced to compress or tamp the sealant 2, e.g., against the positioning element 46. Optionally, the advancer member 30 may include one or more markers 33, e.g., on or adjacent the proximal end 32, and the advancer member 30 may be advanced into the puncture 90 a desired distance, which may be confirmed by monitoring the markers 33. In addition or alternatively, the positioning member 14 may include a second feature (not shown) over which the advancer member 30 may pass when advanced a predetermined distance. The second feature may provide an audible confirmation that the advancer member 30 has been advanced the predetermined distance (in addition or instead of the visible confirmation provided by the markers 33). In addition, the second detent 41b may ensure that the advancer member 30 is not subsequently withdrawn once advanced the predetermined distance.

Figure 3G:
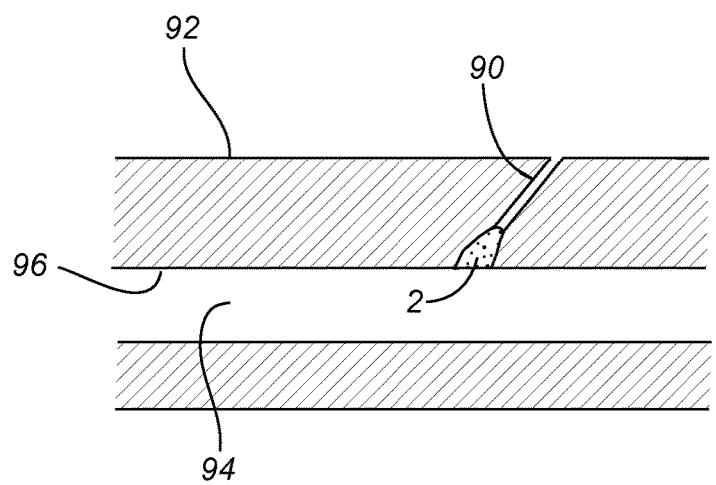

Once the sealant 2 has been exposed for sufficient time and/or tamped by the advancer member 30, the positioning element 46 may be collapsed, and the positioning member 14 withdrawn from the vessel 94 and puncture 90, e.g., pulling the collapsed positioning element 46 through the sealant 2 and advancer member 30, as shown in FIG. 3F. The advancer member 30 may be maintained substantially stationary during withdrawal of the positioning member 14, e.g., to prevent migration and/or dislodgment of the sealant 2 within the puncture 90. Once the positioning member 14 is completely removed, the advancer member 30 may be removed from the puncture 90, leaving the sealant 2 within the puncture 90, as shown in FIG. 3G.

Optionally, after removing the positioning member 14, liquid hydrogel or other sealing compound, or other material may be delivered into the puncture 90, e.g., above and/or around the sealant 2, to assist in achieving hemostasis. For example, such material may be delivered via the lumen 36 of the advancer member 30 and/or by introducing another delivery device (not shown) into the puncture 90, e.g., after removing the advancer member 30.

With additional reference to FIG. 1, with the freeze-dried hydrogel proximal section 4 of the sealant 2 delivered into the puncture 90 adjacent vessel 94, hydration may occur substantially immediately as the sealant 2 is exposed from the tubular member 20 and begins to uptake local fluids (blood or interstitial fluids). For example, the proximal section 4 of the sealant 2 may begin to swell rapidly such that the swelling and the increase in the radial dimension of the proximal section 4 substantially fills a portion of the available space in the puncture 90 above the vessel 94, e.g., above the arteriotomy in the vessel wall. The end result is a discrete, optimally targeted deposition of hydrogel sealant 2 that provides a seal over the arteriotomy.

In addition, the non-freeze-dried distal section 6 of non-crosslinked precursors absorbs local fluids, which initiates crosslinking in-situ and results in a more secure mechanical hold on the surrounding tissue as the freeze-dried hydrogel conforms to the spaces in the tissue tract. Optionally, if the sealant 2 includes salts or other pH adjusting agents, exposure of the sealant 2 may dissolve the agent(s) in the local fluids, which may enhance or facilitate crosslinking of the precursors.

In an exemplary, if the sealant 2 is compressed against the arteriotomy over the vessel 94, the distal section 6 may bond to the outer surface of the vessel wall 96 and/or other tissue adjacent the arteriotomy, or may fill or otherwise penetrate into the arteriotomy, e.g., optionally extending into the interior of the vessel 94, which may enhance the resulting seal and/or prevent migration of the proximal section 4 of the sealant 2, e.g., away from the arteriotomy and vessel wall 96. Thus, the end result may be a discrete, optimally targeted deposition of hydrogel sealant that provides a durable seal over or within the arteriotomy, as shown in FIG. 3G.

Several alternative embodiments of sealants are shown in FIGS. 4-11 and described below that may be delivered, e.g., using the apparatus and methods described elsewhere herein and/or in the references incorporated by reference herein. The sealants described below may be formed from any of the materials and methods described above for sealant 2.

For example, turning to FIGS. 4A and 4B, an exemplary embodiment of a sealant 102 is shown that includes a proximal section 104 of freeze-dried hydrogel and a distal section 106 of non-crosslinked precursors, generally similar to other embodiments herein. In an exemplary embodiment, uncoated biomaterial, e.g., freeze-dried hydrogel, may be rolled or otherwise formed, similar to other embodiments described herein, for the proximal section 104. Thus, the sealant 102 may include a lumen (not shown) extending longitudinally between the proximal and distal sections 104, 106, e.g., to allow delivery of the sealant 102 over a positioning member 40, similar to other embodiments herein.

As shown in FIG. 4A, a cylindrical plug or bolus 106 of substantially dry non-crosslinked hydrogel precursors may be fused or otherwise provided on or adjacent the distal end of the proximal section 104. For example, the distal section 106 may be a solid mass or plug, e.g., a melted and solidified form attached to the proximal section 104, similar to the processes described above. Alternatively, the distal section 106 may be a bolus of powder provided adjacent but separate from the proximal section 104, e.g., sintered or otherwise compressed together, while remaining in a powder form, or simply loaded into a delivery cartridge distal to the proximal section 104 such that the powder is released when the sealant 102 is delivered from the cartridge. For example, if the precursor powder is sintered into a desired shape, the powder particles may behave as a solid mass yet may easily separate from one another, e.g., when delivered within a puncture, which may increase surface contact between the powder and physiologic fluids, which may accelerate and/or otherwise enhance crosslinking of the precursors.

Optionally, the non-crosslinked precursors of the distal section 106 and/or the uncoated biomaterial of the proximal section 104 may have salts or other pH adjusting agents impregnated therein or applied thereto such that, when physiological fluids wet the biomaterial and/or unreacted hydrogel precursors, a favorable pH may be obtained for cross-linking the distal section 106. The ratio of the lengths of unreacted hydrogel precursors to uncoated biomaterial, i.e., distal to proximal sections 106, 104, may range from 0-100% for the respective materials, and the length of the overall sealant 102 may vary, similar to other embodiments herein.

During use, the sealant 102 may be advanced into position, e.g., over a positioning member 40 and/or towards a positioning element 46, in apposition to the surface 96 of an artery at the arteriotomy within a puncture (not shown), e.g., using apparatus and methods similar to those described elsewhere herein. The local fluids within the puncture may initiate crosslinking of the precursors of the distal section 106, which may cause the crosslinking precursors to soften, flow into available space within the puncture, e.g., into the arteriotomy and/or into the vessel itself, and begin to cross-link to form a hydrogel. The "setting" action of the non-crosslinked precursors as the in-situ crosslink occurs may act as a glue to substantially fix the sealant 102 in position over the arteriotomy.

The distal section 106 may also form a patch over the arteriotomy, e.g., against or into the vessel wall 96, e.g., with the sealant 102 acting as a sponge to absorb any blood in the immediate area, e.g., to minimize subsequent oozing. For example, as shown in FIG. 4B, the distal section 106 may be compressed against the vessel wall 96, e.g., using a tamping member (not shown), similar to other embodiments herein, which may cause deformation of the crosslinking precursors, potentially enhancing the coverage area of the adherent material and/or increasing the surface area for the cross-linking reaction.

Turning to FIGS. 5A and 5B, an alternative embodiment of a sealant 102' is shown that includes a proximal section 104' and a distal section 106' generally similar to the sealant 102 of FIGS. 4A and 4B. However, as shown in FIG. 5A, unlike the previous embodiment, the proximal section 104' may include a pocket 104d' formed in the distal end of the uncoated biomaterial within which the non-crosslinked precursors of the distal section 106' may be formed or deposited. For example, a solid mass of non-crosslinked precursors or a bolus of precursor powders may be loaded into the pocket 104d,' e.g., loosely or fused to the distal end of the first section 104a,' similar to previous embodiments.

As shown in FIG. 5B, the sealant 102' may be compressed within a puncture and/or against an arteriotomy in the vessel wall 96, similar to other embodiments herein, which may cause an annular wall of the first section 104' defining the pocket 104d' to splay out over the flattened distal section 106,' e.g., providing improved adhesion between the uncoated biomaterial of the proximal section 104' and the adherent material of the distal section 106.'

Turning to FIGS. 6A-6C, another alternative embodiment of a sealant 102" is shown, similar to the sealant 102' of FIGS. 5A and 5B (or the sealant 102 of FIGS. 4A and 4B) including a proximal section 104" of freeze-dried hydrogel and a distal section 106" of non-crosslinked polymers. Similar to the sealant 102,' the proximal section 104" includes a pocket 104d" for receiving the non-crosslinked precursors of the distal section 106." Unlike the previous embodiments, the proximal section 104" may include one or more longitudinal slits 104e" formed laterally through the uncoated biomaterial and extending only partially between and spaced apart from the proximal and distal ends of the proximal section 104." Such a slit 104e" through the side of the proximal section 104" may facilitate collapsing the sealant 102" during compression, e.g., into a "lantern" shaped body, as shown in FIGS. 6B and 6C. For example, these drawings show how compression may result in a substantially flattened low profile for the delivered sealant 102," which may provide maximum surface area coverage against the vessel wall 96.

Figure 7A:
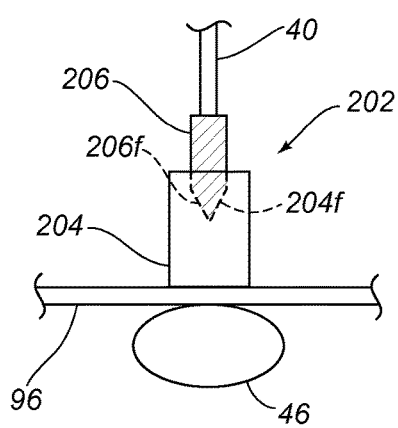
FIGS. 7A and 7B are side views of a fourth alternative embodiment of a sealant being compressed against an arteriotomy, e.g., using the apparatus and methods of FIGS. 2A-3G.
Figure 7B:
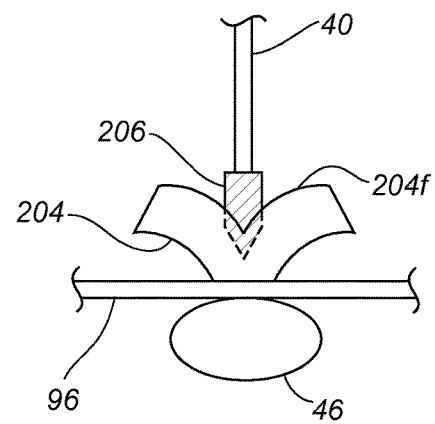

Turning to FIGS. 7A and 7B, still another embodiment of a sealant 202 is shown that includes two distinct sections of sealant material. The distal section 204 may be formed from a relatively softer, rapidly swelling composition, e.g., freeze-dried hydrogel, while the proximal section 206 may be formed from a relatively harder, slower swelling composition. As shown, the proximal section 206 may be nested to some degree into the distal section 204, e.g, including a tapered distal tip 206f that is initially provided within a similar shaped pocket 204 in the proximal end of the distal section 204, as shown in FIG. 7A.

The act of placing a compressive load on the proximal section 206 of the sealant 202 while holding the distal face of the distal section 204 substantially fixed (e.g., in this case using a balloon 46 as a backstop), may drive the proximal section 206 into the distal section 204. As shown in FIG. 7B, this action may expand the distal section 204 into a shape that is wider than its original configuration. For example, as shown in FIG. 7B, the distal section 204 may be designed to split during compression, bulge, or otherwise deform under the compressive load.

Figures 8A, 8B, 8C:
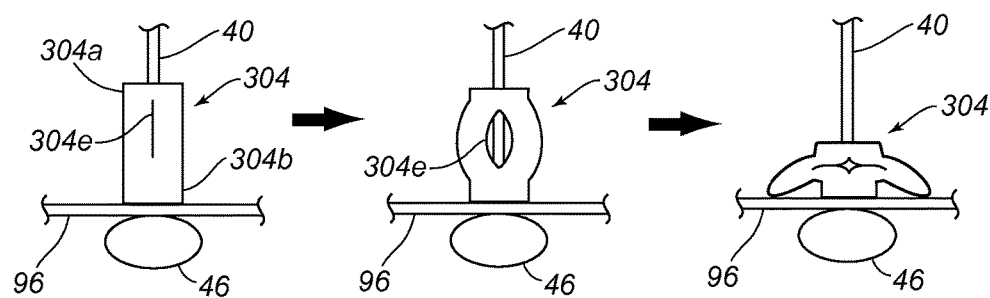
FIGS. 8A-8C are side views of a fifth alternative embodiment of a sealant being compressed against an arteriotomy, e.g., using the apparatus and methods of FIGS. 2A-3G.

Turning to FIGS. 8A-8C, still another embodiment of a sealant 304 is shown that includes a proximal end 304a, a distal end 304b and a longitudinal slit 304e extending partially between the proximal and distal ends 304a, 304b, e.g., similar to the proximal section 104" of the sealant 102" of FIGS. 6A-6C. In this embodiment, the freeze-dried hydrogel or other sealant may include one or more slits to enable a controlled deformation of the sealant 304 under a compressive load. For example, the sealant 304 may include two longitudinal slits 304e (only one visible in the side view shown in FIG. 8A), e.g., offset one hundred eighty degrees (180°) apart from one another around the circumference of the sealant 304. Alternatively, the number and/or orientation of the slits 304e may be modified, e.g., to attain a desired morphology after compression.

It will be appreciated that the shape of any of the sealants herein may be modified to have a shape that is conducive to controlled deformation. Examples include an inverted golf tee, an hourglass, swept or wavy surfaces, and the like.

Figure 9:
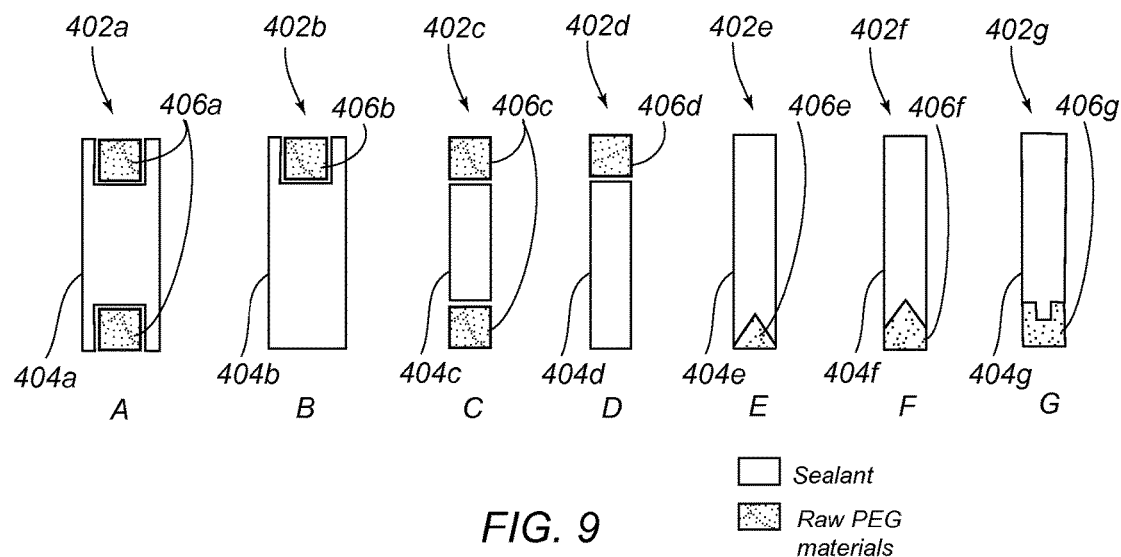
FIG. 9 includes side views of additional alternative embodiments of sealants including a freeze-dried hydrogel section and one or more non-crosslinked precursor sections.

Turning to FIG. 9, additional alternative embodiments of sealants are shown that include non-crosslinked precursor sections 406a-406g and freeze-dried hydrogel main sections 404a-404g. The location of the non-crosslinked precursors 406a-406g may be proximal to, distal to, or both proximal and distal to the hydrogel main sections 404a-404g. The precursors 406a-406g may be provided as a solid mass fused or otherwise attached to the main section 404a-404g or as a bolus of powder, similar to other embodiments herein. For example, a sealant 402a may be provided that includes precursor sections 406a within pockets in both proximal and distal ends of the main section 404a, while the sealant 402b may include a precursor section 406b within a pocket on the proximal end of the main section 404b.

Sealants 402c and 402d include a main section 404c, 404d, e.g., formed from freeze-dried hydrogel, and non-crosslinked precursor sections on either both ends 406c or one end 406d of the main section 404c, 404d. In these embodiments, the non-crosslinked sections 406c, 406d may be a solid mass fused to the main sections 404c, 404d or a bolus or sintered mass of precursor powders.

Sealants 402e-402g include main sections 404e-404g, e.g., formed from freeze-dried hydrogel, and distal sections 406e-406g, e.g., solid masses of non-crosslinked precursors fused or otherwise attached to the main sections 404a-404g. For example, in sealant 402e, the main section 404e may include a recess, e.g., a conical recess in one end for receiving the distal section 406e substantially flush with the end of the main section 404e. Alternatively, the distal section 406f may extend from the recess in the main section 404f, as shown for the sealant 402f. In a further alternative, the sealant 402g includes a smaller tab or other feature extending from the main section 404g around which the distal section 406g may be formed and/or extend.

Figure 10A:
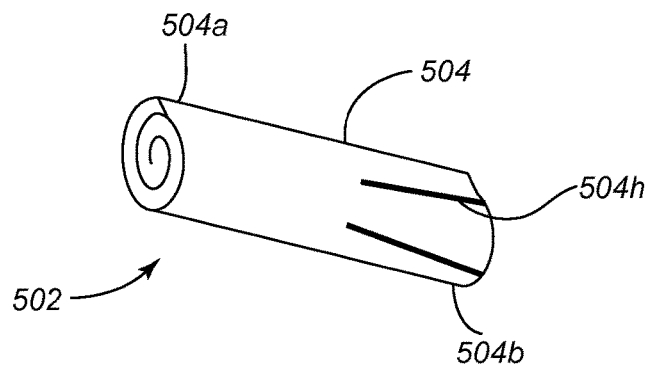
FIGS. 10A-10C are perspective views of another embodiment of a sealant, showing a method for creating an adhesive coating on a base section of material to provide the sealant.
Figure 10B:
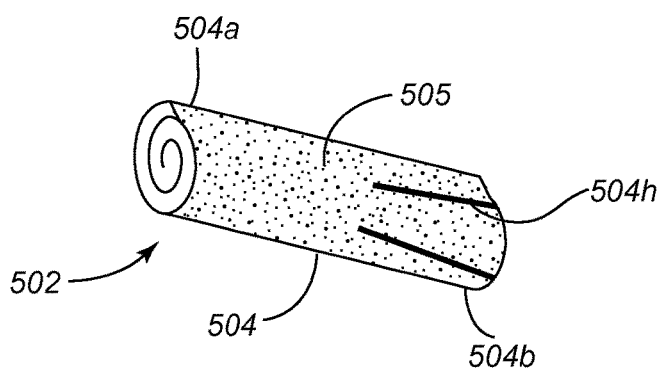
Figure 10C:
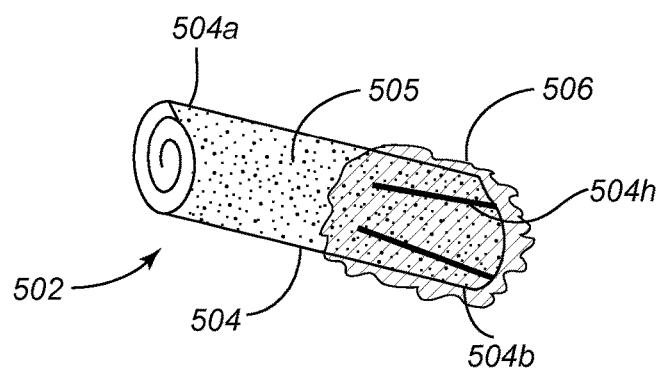
Figure 10D:
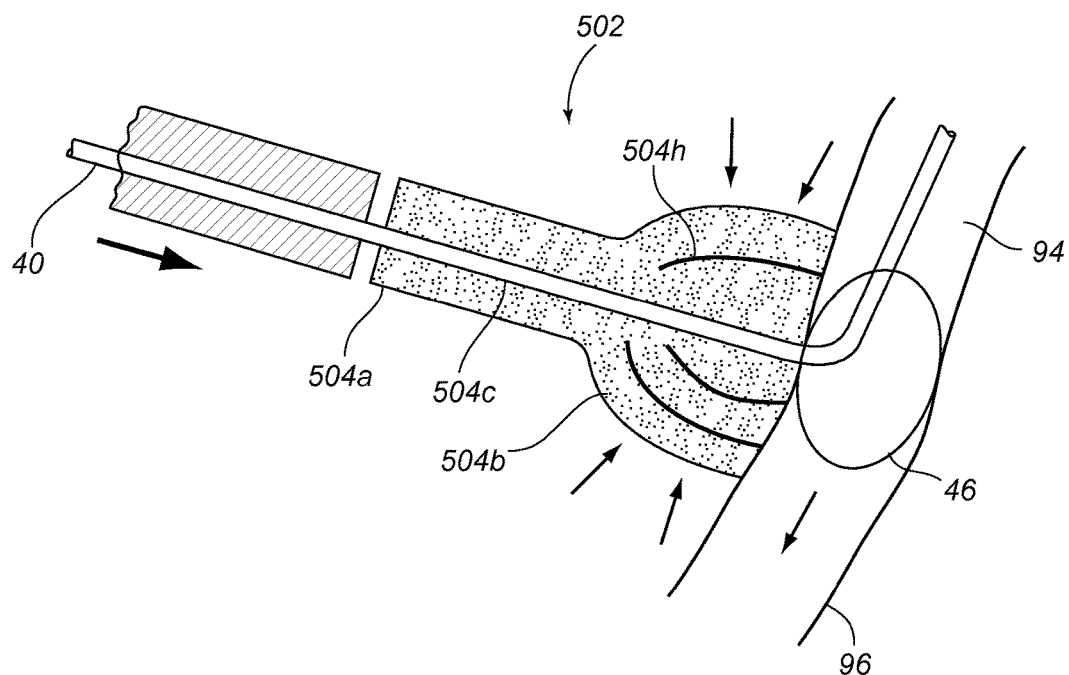
FIG. 10D is a cross-sectional view of a patient's body showing a method for sealing a puncture using the sealant of FIGS. 10A-10C.

Turning to FIGS. 10A-10D, another embodiment of a sealant 502 is shown, which may include a section of rolled hydrogel or other base material 504, such as any of the materials described above, including proximal and distal ends 504a, 504b. A plurality of slits 504h may be formed in the distal end 504b, e.g., by mechanical cutting, laser cutting, stamping, and the like, as shown in FIG. 10A. The distal end 504b may then be coated, e.g., with non-crosslinked precursors 506, as shown in FIG. 10C, similar to other embodiments herein and in the references incorporated by reference herein. Optionally, pH controlling salts and the like may be embedded in the coating or in the non-coated biomaterial, e.g., as shown in FIG. 10B. The slits 504h may facilitate collapsing the coated end 504b of the sealant 502, e.g., resulting in a wider footprint to cover an arteriotomy or other vessel puncture, as shown in FIG. 10D. The sealant 502 may be delivered using apparatus and methods similar to those described elsewhere herein.

Figure 11A:
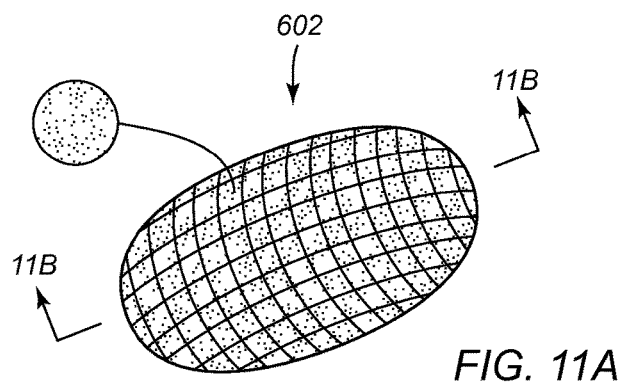
FIG. 11A is a perspective view of an exemplary embodiment of a patch for sealing a puncture in tissue.
Figure 11B:
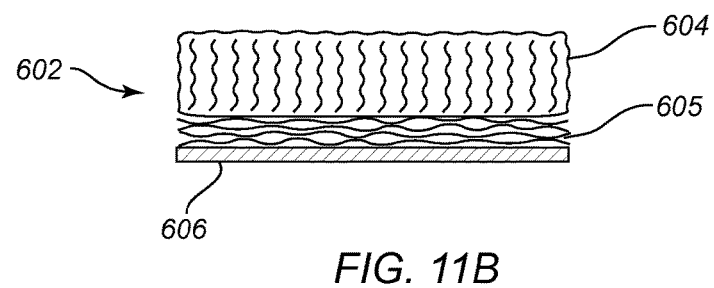
FIG. 11B is a cross-sectional view of the patch of FIG. 11A taken along line 11B-11B.

Turning to FIGS. 11A and 11B, an exemplary embodiment of a pliable patch-like material 602 is shown, e.g., having lateral dimensions (from the perspective of FIG. 11A), e.g., a width, height, diameter, and the like depending on the desired shape for the patch, formed from material with minimal stretch in the lateral directions. The patch 602 may include a weave or other arrangement 605 of synthetic biocompatible and/or bioresorbable fibers, such as PLG, PLA or PGA, e.g., defining a first or base layer, as shown in FIG. 11B. Alternatively, the patch 602 may also be formed from naturally occurring proteins, such as collagen, or other bioabsorbable materials, such as those described above.

As shown in FIG. 11B, the patch 602 may be covered on one or both sides with non-crosslinked precursors, similar to other embodiments herein, e.g., to provide an adhesive layer 606 for the patch 602. As shown, the coating 606 has been provided on only the bottom side of the base layer 605 of the patch 602. In the case of coating 606 on only one side, a layer 604 of freeze-dried hydrogel or other expandable, bioabsorbable material may be provided on the top side of the base layer 605, e.g., to absorb excess fluid and/or expand to fill a space above the delivery site. Optionally, salts to control the pH (not shown) may be blended with the coating 606, embedded in the base material 605, embedded in the freeze-dried hydrogel 604, and/or dissolved in a buffer solution that is used to saturate the assembly immediately before or after the patch 602 is applied to a arteriotomy or other tissue surface.

The patch 602 may be delivered using the apparatus and methods described elsewhere herein, e.g., where the patch 602 is small enough to be loaded into a cartridge. Alternatively, the patch 602 may be applied manually, e.g., if the tissue surface is sufficiently exposed.

For example, upon application to a vessel or other tissue surface or structure, e.g., over an arteriotomy or other puncture (not shown), adhesion to the vessel may occur due to the coating 606, but the non-stretch nature of the base layer 605 of the substrate patch 602 may prevent the expanding pressurized vessel from substantially opening or enlarging the arteriotomy because of the lateral resistance of the patch 602 to expansion. The dense weave of the base layer 605 and the cross-linking of the coating 606 may prevent blood or other fluid from the vessel from leaking though the patch 602. The size of the patch 602 may vary from being large enough to surround all or a portion of vessel having a puncture therethrough, e.g., adhering the patch all around the puncture to only pulling together the mid-point of the vessel puncture for achieving substantial hemostasis. Optionally, after applying the patch, another hemostatic material, such as freeze-dried hydrogel (or any other sealant, such as those described elsewhere herein) may be applied over the top to achieve complete hemostasis.

In still another embodiment, a plurality of coated sealant pellets (not shown) may be provided for sealing a puncture through tissue. For example, freeze-dried hydrogel sealant may be used as a carrier for non-crosslinked PEGs or other precursors in a solid (i.e., melted, mixed, and solidified) form, e.g., a solid shell surrounding the underlying freeze-dried hydrogel. For example, freeze-dried hydrogel sealant may be punched, ground, or other formed into particles, e.g., having one or more diameters between about 0.5-10 millimeters. The particles may then be spray-coated with a hot liquid mass, e.g., including the melted PEG amine and PEG ester. The resulting pellets may then be delivered over an arteriotomy, into a puncture, or applied to a tissue surface, e.g., as a bolus through a sheath or other delivery device, and the non-crosslinked precursors may reconstitute and bind to form a slurry of adhesive gel and rapidly-absorbing hydrogel sealant over the arteriotomy, within the puncture, and/or onto the tissue surface.

It will be appreciated that elements or components shown with any embodiment herein are merely exemplary for the specific embodiment and may be used on or in combination with other embodiments disclosed herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A method for making a sealant for sealing a puncture through tissue, comprising:
    forming an elongate rolled proximal section including a proximal end, a distal end, an exterior side surface therebetween, and a cross-section sized for delivery into a puncture through tissue, the rolled proximal section formed from a freeze-dried hydrogel that expands when exposed to physiological fluid within a puncture; and
    fusing a solid mass of non-crosslinked hydrogel precursors onto a cross-sectional face of the distal end of the rolled proximal section, to form a distal section fused onto the cross-sectional face of the distal end of the rolled proximal section, the precursors remaining in an unreactive state until exposed to an aqueous physiological fluid, whereupon the precursors undergo in-situ crosslinking with one another to adhere to the puncture.

2. A method for making a sealant for sealing a puncture through tissue, comprising:
    forming a sheet of a freeze-dried hydrogel that expands when exposed to physiological fluid within a puncture;
    rolling the sheet into a tubular roll including a proximal end, a distal end, and a lumen extending between the proximal and distal ends;
    loading the tubular roll into a tubular member such that the distal end of the tubular roll is offset inwardly from a first end of the tubular member;
    melting a plurality of non-crosslinked hydrogel precursors, the precursors remaining in an unreactive state until exposed to an aqueous physiological fluid, whereupon the precursors undergo in-situ crosslinking;
    applying the melted precursors to a cross-sectional face of the distal end of the tubular roll within the tubular member; and
    allowing the melted precursors to solidify to create a solid mass fused to the cross-sectional face of the distal end of the tubular roll resulting in a sealant having a proximal section comprising the tubular roll and a distal section comprising the solid mass of precursors.

3. The method of claim 1, further comprising melting PEG-amine and PEG-ester powders into a liquid mixture of non-crosslinked PEG precursors, and wherein fusing a solid mass of non-crosslinked hydrogel precursors onto the cross-sectional face of the distal end comprises using a vacuum generator to apply the liquid mixture of non-crosslinked PEG precursors onto the distal end.

4. The method of claim 3, wherein the liquid mixture is applied onto the cross-sectional face of the distal end within a substantially dry environment.

5. The method of claim 4, wherein the liquid mixture cools and solidifies into a solid mass fused to the cross-sectional face of the distal end.

6. The method of claim 1, wherein forming the elongate rolled proximal section comprises:
    forming a sheet of the freeze-dried hydrogel; and
    rolling the sheet into a tubular roll including a lumen extending between the proximal and distal ends.

7. The method of claim 6, wherein rolling the sheet comprises loading the sheet into a tubular member to create the tubular roll, and wherein a vacuum generator draws a liquid mixture of non-crosslinked PEG precursors into the tubular member to apply the liquid mixture to the cross-sectional face of the distal end.

8. The method of claim 1, wherein fusing a solid mass of non-crosslinked hydrogel precursors onto the cross-sectional face of the distal end comprises:
    providing the precursors in a solid state;
    melting the precursors to a liquid state;
    applying the melted precursors to the cross-sectional face of the distal end of the proximal section; and
    allowing the melted precursors to solidify to create the solid mass.

9. The method of claim 8, wherein the melted precursors are applied to the cross-sectional face of the distal end using a vacuum.

10. The method of claim 8, wherein the precursors are melted and applied onto the cross-sectional face of the distal end within a substantially dry environment.

11. The method of claim 1, further comprising including one or more reinforcement elements in the distal section.

12. The method of claim 2, wherein a vacuum generator is used to draw the melted precursors into the tubular member to apply the melted precursors to the cross-sectional face of the distal end.

13. The method of claim 2, further comprising placing one or more reinforcement members within the first end of the tubular member before applying the melted precursors such that the one or more reinforcement members are embedded in the solid mass.

14. The method of claim 13, wherein the one or more reinforcement members comprise a mesh.

15. The method of claim 13, wherein the one or more reinforcement members comprise one or more filaments wound helically into the first end of the tubular member.

16. The method of claim 2, further comprising:
providing a plurality of precursors in a solid state; and
mixing the solid precursors together before melting the precursors.

17. The method of claim 16, further comprising mixing one or more pH adjusting agents with the solid precursors before melting the precursors.

18. The method of claim 2, further comprising mixing one or more diluents with the melted precursors before applying the melted precursors to the distal end to enhance one or more mechanical properties of the resulting solid mass.

19. The method of claim 2, further comprising coating, embedding, or impregnating one or more pH adjusting agents in an outer surface of the solid mass.

20. The method of claim 2, wherein the precursors are melted and applied onto the cross-sectional face of the distal end within a substantially dry environment.

21. The method of claim 2, further comprising a step of loading the tubular member containing the sealant therein into a delivery apparatus for delivery into the puncture.

22. The method of claim 2, wherein the tubular member is sized such that its length can accommodate the sealant.

* * * * *